United States Patent [19]

Ohkuma et al.

[11] Patent Number: 5,364,652
[45] Date of Patent: Nov. 15, 1994

[54] INDIGESTABLE DEXTRIN

[75] Inventors: Kazuhiro Ohkuma, Sanda; Yoshio Hanno, Itami; Kazuyuki Inada, Takarazuka; Isao Matsuda, Itami; Yasuo Katta, Hyogo, all of Japan

[73] Assignee: Matsutani Chemical Industries Co., Ltd., Hyogo, Japan

[21] Appl. No.: 967,119

[22] Filed: Oct. 27, 1992

[30] Foreign Application Priority Data

Oct. 29, 1991 [JP] Japan .................................. 1-311846

[51] Int. Cl.$^5$ ............................................. A23L 1/0522
[52] U.S. Cl. .................................... 426/549; 426/590; 426/658
[58] Field of Search ........................ 426/549, 658, 590

[56] References Cited

U.S. PATENT DOCUMENTS 4,247,568  1/1981  Carrington ........................ 426/661

*Primary Examiner*—Donald E. Czasa
*Assistant Examiner*—Mary S. Mims
*Attorney, Agent, or Firm*—Sughrue, Mion, Zinn, Macpeak & Seas

[57]   ABSTRACT

An indigestible dextrin characterized in that the dextrin is prepared by heat-treating potato starch with addition of hydrochloric acid thereto to obtain a pyrodextrin, hydrolyzing the pyrodextrin with alpha-amylase and glucoamylase and removing at least one-half of glucose formed from the resulting hydrolyzate, and comprises a fraction other than glucose.

14 Claims, 9 Drawing Sheets

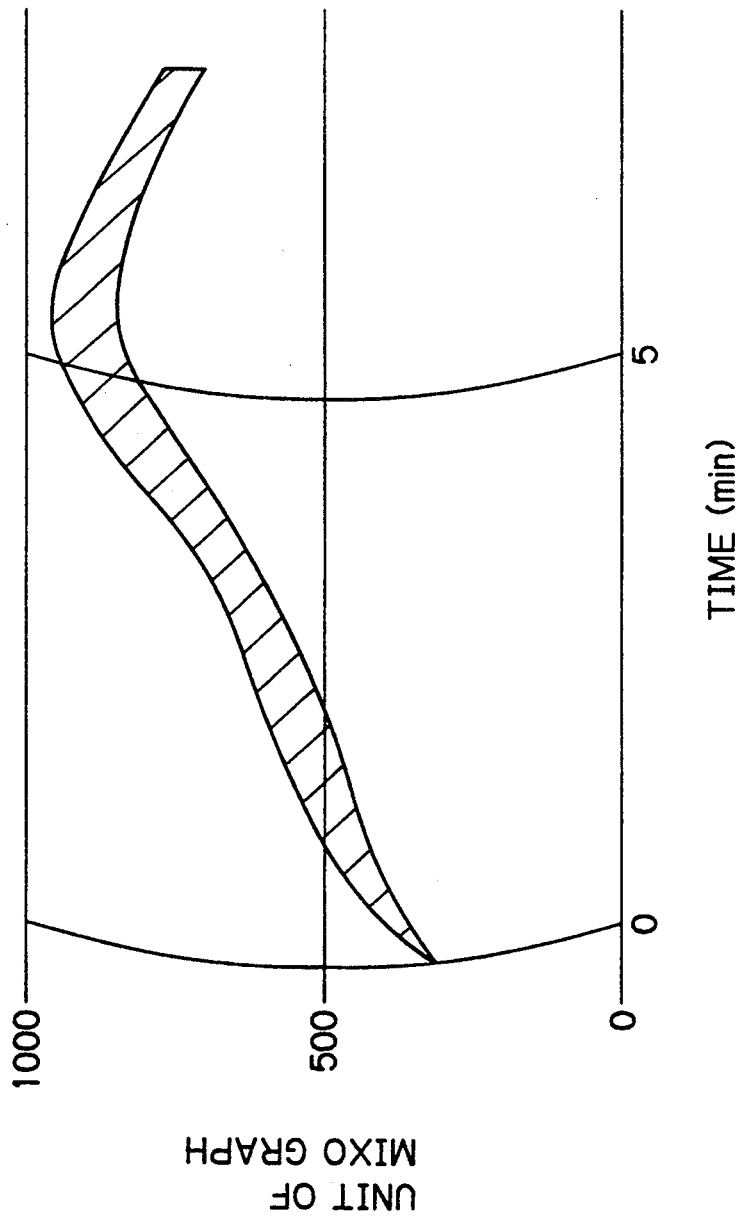

INDIGESTABLE DEXTRIN

BACKGROUND OF THE INVENTION

1. Field of the Invention

The present invention relates to indigestible dextrins which are prepared by heat-treating potato starch with addition of an acid and hydrolyzing the resulting starch with alpha-amylase and glucoamylase and which contain dietary fiber and have a low caloric value.

2. Description of the Prior Art

Pyrodextrins are prepared by heating a starch containing several percent of water in the presence or absence of acid. These dextrins include British gum which is obtained by heating the starch at 135° to 218° C. in the absence of acid for 10 to 20 hours, white dextrin which is prepared by heating the starch at 79° to 121° C. in the presence of acid for 3 to 8 hours, and yellow dextrin which is prepared similarly by heating the starch at 150° to 220° C. with addition of acid for 6 to 18 hours.

It is known that these dextrins are consisted of glucose, the component of starch, which consists primarily of 1→4 and 1→6 glycosidic linkages and contains very small amounts of 1→3 and 1→2 glycosidic linkages.

The proportions of these glycosidic linkages are disclosed only in J. D. Geerdes et al., J. Am. Chem. Soc., Vol. 79, 4209 (1957), G. M. Christensen et al., J. Am. Chem. Soc., Vol. 79, 4492(1957) and the literature mentioned below. Methylation analysis of pyrodextrin obtained by heat-treating commercial corn starch with addition of hydrochloric acid reveals that the pyrodextrin comprises at least 57.3% of 1→4 glycosidic linkage fraction (2,3,6-Tri-O-Methyl-D-glucose), 2.6% of 1→6 glycosidic linkage fraction (2,3,4-Tri-O-Methyl-D-glucose), up to 1.2% of 1→3 glycosidic linkage fraction (2,4,6-Tri-O-Methyl-D-glucose), 6.3% of a fraction having both 1→4 and 1→6 linkages (2,3-Di-O-Methyl-D-glucose) and about 20% of a fraction having other glycosidic linkages.

Further R. L. Whistler and E. F. Paschall, Starch Chemistry & Technology, Vol. 1, 430 (965) makes reference to analyzed values of linkage types constituting heat-treated amylopectin and heat-treated amylose which were obtained by separating corn starch into amylopectin and amylose fractions and individually heating the fractions with addition of an acid. The analyzed values were obtained for the heat-treated fractions which were prepared by gelatinizing the starch, then separating the starch into the two fractions and heating the fractions. The form of powder heat-treated therefore differs from that of natural starch, so that the values can not be used directly for comparison. However, in view of the fact that the ratio between the two fractions of usual corn starch is about 8:2, the analyzed values, when calculated for corn starch, correspond to 67% of 1→4 glycosidic linkage fraction-(2,3,6-Tri-O-Methyl-D-glucose), 2.7% of 1→3 glycosidic linkage fraction (2,4,6-Tri-O-Methyl-D-glucose) and 7.8% of a fraction having both 1→4 and 1→6 glycosidic linkages (2,3 Di-0-Methyl-D-glucose).

Tomasik, P. and Wiejak, S., Advance in Carbohydrate Chemistry, Vol. 47, 279-343 (1990) generally describes the latest information as to processes for preparing pyrodextrins.

When analyzed, however, any of commercial pyrodextrins was found to be up to 30% in indigestible content, up to 3% in dietary fiber content, at least 3.1 kcal/g in caloric value 1 and at least 3.1 kcal/g in caloric value 2. When starch was heated under altered conditions to increase these contents, it was possible to increase the indigestible content to about 60% and the dietary fiber content to about 30% and to decrease the caloric value 1 to about 2.7 kcal/g and the caloric value 2 to about 2 kcal/g, whereas the product then contained an increased amount of colored substance, had a stimulative odor, therefore required refining and was not practically useful because of extreme difficulties encountered in refining the product. Accordingly, it is impossible to obtain a dextrin which is at least 75% in indigestible content, at least 20% in dietary fiber content, up to 2.6 kcal/g in caloric value 1 and up to 2 kcal/g in caloric value 2 as contemplated by the present invention.

With respect to the enzymic hydrolysis of pyrodextrins, B. Brimhall, Ind. Eng. Chem., 36, 72 (1944) discloses that when so-called British gum prepared by heating starch in the absence of acid is hydrolyzed with alpha-amylase, the limit of decomposition is 3.5% calculated as maltose, i.e., about 7.4 calculated as DE.

Further U.S. Pat. No. 3,974,032 discloses a hydrolyzate which is prepared from a pyrodextrin obtained with addition of hydrochloric acid and having a degree of branching of 7 to 16% by hydrolyzing the pyrodextrin at 60° to 85° C. To DE of 9 to 20 with alpha-amylase and which is up to 20 in the ratio of weight average molecular weight to number average molecular weight and contains up to 20% of oligosaccharides having a degree of polymerization of 200. However, the patent discloses nothing about hydrolysis with glucoamylase or about dietary fiber.

With improvements in living standards in Japan in recent years, eating habits have changed and become similar to those of American and European people. This trend has resulted in a lengthened average life span and a rapidly aging society with marked increases in degenerative diseases. Manifestly, people have become health-oriented. Attention has, therefore, been directed to dietary fibers and oligosaccharides enhance the function of foods and livestock feeds in that these materials are known to alleviate constipation and other desired biological regulatory functions.

Indigestible substances, such as dietary fibers and oligosaccharides, exhibit various modes of behavior in the digestive tracts producing physiological effects on the living body. First in the upper digestive tract, water-soluble dietary fibers slow the transport of food and delay the absorption of nutrients. Delayed absorption of sugar, for example, suppresses the rise in blood sugar value, consequently lowering insulin requirements. Further, excretion of bile acid is promoted, diminishing the sterol group in the body thereby lowering the cholesterol level of the serum. Other physiological effects through the endocrine system of the body are also reported.

Another feature of these indigestible substances is they are not digested or absorbed by the digestive tract, including the small intestine and reach the large intestine. On reaching the large intestine, oligosaccharides and dietary fibers are partly acted on by enterobacteria yielding short-chain fatty acids, intestinal gases, vitamins, etc. Acidification of the intestinal environment by the short-chain fatty acids condition the intestine. It has also been reported that when absorbed, these short-chain fatty acids are metabolized to provide energy and, simultaneously, inhibit the synthesis of cholesterol.

Therefore, ingestible substances are necessary in obtaining these desired physiological effects.

A "dietary fiber hypothesis" suggested by Trowell and Burkitt epidemiologically revealed that there is a negative correlation between the intake of dietary fibers and the onset of non-infectious diseases such as cholelithiasis, ischemic heart diseases, cancer of the large intestine, etc. Thus, insufficient ingestion of dietary fibers is thought to be a cause of degenerative diseases which are said to be diseases of the Western type. The dietary fibers are defined as the "whole group of indigestible components of foods which are not digestible by human digestive enzymes" and are classified into insoluble dietary fibers and water-soluble dietary fibers according to the solubility in water. Of these, water-soluble dietary fibers have attracted attention as materials for functional foods and livestock feeds because of their great physiological function.

For example, it is said that high viscosities inhibit diffusion of sugar, resulting in delayed absorption o sugar and reduction in the rise of blood sugar value, consequently lowering insulin necessity. Further it is said that promoted excretion of bile acid into feces by water-soluble dietary fibers diminishes cholesterol in the serum, and that after reaching the large intestine, the dietary fibers are acted on by enterobacteria to produce lactic acid and acetic acid with these organic acids lowering the pH within the large intestine and preventing cancer of the large intestine.

Examples of such water-soluble dietary fibers include guar gum, glucomannan, pectin and like natural gums which have high viscosity which are difficult to ingest singly in a large amount. Further the addition of these fibers to processed foods encounters problems in preparing the food and presents difficulties with respect to texture. It has therefore long been desired to provide dietary fibers of low viscosity which have the same physiological functions as the above fibers, are easy to ingest and are user-friendly in preparing processed foods.

In recent years in Japan, processed foods, precooked foods, fast foods and the like have found wider use with the maturity of economical environments and the resulting improvements in food processing techniques and distribution techniques. With this trend, diversified information as to the ingestion of foods has become available, and eating habits to fulfill the nutrient requirements are changing to health-oriented dietary habits contemplated for the prevention of nutrition disorders and degenerative diseases due to eating habits. Especially, people of middle or advanced age and young women have much need for low caloric foods, so that low caloric sweeteners and bulking agents for strong sweetening agents have been developed. Among these, low caloric sweeteners include various indigestible oligosaccharides and sugar alcohols, which nevertheless have many problems with respect to the quality, degree of sweetness, oligosaccharide content and likelihood of causing laxation.

The bulking agent available for use with strong sweetening agents such as aspartame is polydextrose only, whereas polydextrose is ingestible in a limited amount, tastes bitter in an acid condition, is hygroscopic and therefore has problems. In view of the situation described, it has been desired to provide a low caloric bulking agent which fulfills the requirements for use as a food and which is usable for sweeteners and the like with safety.

On the other hand, starch is used in large quantities in various processed foods as a food material. Useful food materials of these types include starch and starch products such as pregelatinized starch, pyrodextrin, and its derivatives, glucose, corn syrup solids and maltodextrin. However, a majority of these starch products are not higher than 5% in the content of indigestible component and at least 3.9 kcal/g in caloric value, so that among starches and like materials, only pyrodextrin appears useful as a dietary fiber and low caloric material. Heat-treated starch (pyrodextrin) will hereinafter be referred to merely as "dextrin".

SUMMARY OF THE INVENTION

Accordingly, the main object of the present invention is to provide a novel indigestible dextrin which is diminished in the amount of colored substance and stimulative odor and which contains at least 37% of an indigestible component and at least 7.8% of dietary fiber and is up to about 3.1 kcal/g in caloric value 1 and up to about 2.9 kcal/g in caloric value 2. Preferably, the portion of the dextrin other than glucose contains at least about 80% of an indigestible component and at least about 8% of dietary fiber and is up to 2 kcal/g in caloric value 1 and up to 1.5 kcal/g in caloric value 2.

The term "dextrin" used merely as such hereinafter means a heat-treated starch (pyrodextrin).

We conducted research on processes for preparing dextrins, hydrolysis processes and processes for preparing indigestible dextrins from dextrins. Based on the results obtained, we filed a patent application for an invention entitled "Process for Preparing Indigestible Dextrin." Our research subsequently carried out on the physiological activities of this dextrin revealed that the dextrin had an intestine conditioning effect, effect to ameliorating hypercholesterolemia, effect to lower insulin requirements, hypotensive effect and low caloric value, i.e., effects similar to those of dietary fibers. Based on the finding, we filed a patent application for the dextrin as a food composition.

We have also investigated the correlation of the structure of the dextrin with the content o indigestible component or dietary fiber and with the caloric value thereof, and found that the contents of indigestible component and dietary fiber of the dextrin are in inverse proportion to the amount of 1→4 glycosidic linkages in the dextrin among other glycosidic linkages therein, and that the caloric value is in proportion to the amount of 1→4 glycosidic linkages in pyrodextrin among other glycosidic linkages therein. We have further conducted detailed research.

The research thus conducted on various pyrodextrins indicates that the contents of indigestible component and dietary fiber and the caloric value are closely related with the amounts of glycosidic linkages such as 1→4 glycosidic linkages and with the average molecular weight of the dextrin, consequently affording equations representing high degrees of correlation by statistical numerical analysis. However, the commercial pyrodextrins obtained by the prior art are as low as 5 to 30% in the content of indigestible component and 3 to 12% in dietary fiber content and as high as 3.3 to 3.9 kcal/g in caloric value 1 and 3.1 to 3.85 kcal/g in caloric value 2. Although attempts are made to produce an improved pyrodextrin by a longer period o reaction at a high temperature, the product contains a colored substance, releases a stimulative odor and is in no way practically useful.

We have further conducted research to give increased contents of indigestible component and dietary fiber and found the following.

1) When pyrodextrin is hydrolyzed with alpha-amylase and glucoamylase, the resulting glucose and monosaccharides (which consist primarily of glucose and will therefore be referred to as "glucose" hereinafter) can be substantially separated off by ion exchange resin chromatography.
2) When at least one-half of digestible glucose is removed from the hydrolyzate to obtain an indigestible fraction, the fraction contains at least 37% of an indigestible component and at least about 8% of dietary fiber and is up to 2 kcal/g in caloric value 1 and up to about 2.9 kcal/g in caloric value 2.
3) When a greater proportion of glucose is removed from the hydrolyzate to obtain an indigestible fraction, the fraction contains at least 80% of an indigestible component and at least 18% of dietary fiber and is up to 2 kcal/g in caloric value 1 and up to about 1.5 kcal/g in caloric value 2.
4) When disaccharides and oligosaccharides are removed from the hydrolyzate along with glucose, the resulting dextrin can be given a still higher dietary fiber content.

The present invention has been accomplished based on these novel findings.

Accordingly, the foregoing object of the present invention can be fulfilled by determining the structural requirement of the pyrodextrin to be used as the starting material of the invention and by providing an indigestible dextrin by hydrolyzing the pyrodextrin with alpha-amylase and glucoamylase and separating off a digestible fraction from the resulting hydrolyzate by ion exchange resin chromato-graphy.

DETAILED DESCRIPTION OF THE INVENTION

Figure 1:
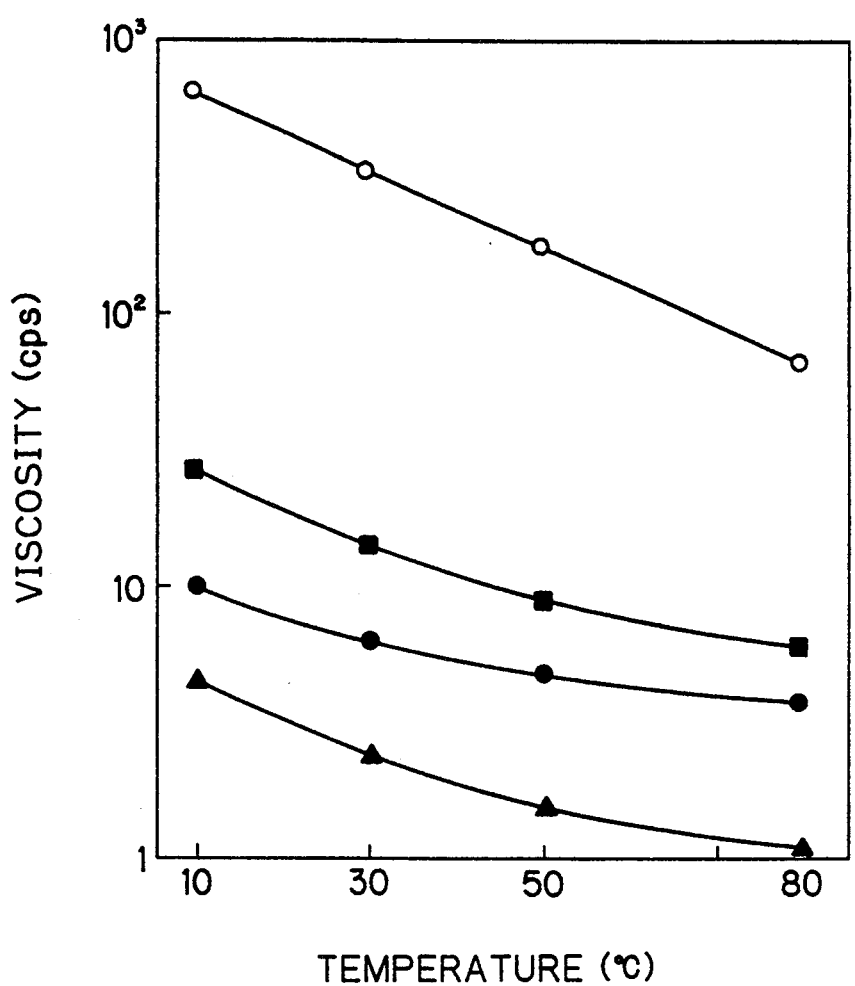

The values of analytical data as to samples (especially those of dextrin for use in the present invention) herein given are those calculated as solids. The number average molecular weight will be abbreviated as MN, the weight average molecular weight as MW, and the ratio of weight average molecular weight to number average molecular weight as MW/MN. Glucose residues having a 1→4 linkage only will be expressed as "glucose residues having a 1→4 linkage," and similar expressions will be used also for 1→6 linkage and 1→3 linkage. The numerical values used for the compositions of food examples and feed examples are those of moisture-containing components. The dietary fiber contents and caloric values given in these examples, except for those of indigestible dextrin, are calculated according to "Tables of Standard Compositions of Japanese Foods," Fourth Edition (edited by Science & Technology Agency, Resources Council, 1982).

The starch to be used for preparing the indigestible dextrin of the invention is potato starch, to which an acid needs to be used as a catalyst. Although various acids are usable, hydrochloric acid is especially preferable to use since the product is used for foods. To meet the requirement for use in foods, the product preferable has higher contents of indigestible component and dietary fiber. Thus, the product should contain at least 37% of an indigestible component and at least about 8% of dietary fiber and should be up to about 3 kcal/g in caloric value 1 and caloric value 2. More preferably, the fraction of the product other than glucose should contain at least 80% of an indigestible component and at least 18% of dietary fiber and should be up to 2 kcal/g in caloric value 1 and up to about 1.5 kcal/g in caloric value 2.

Incidentally, pyrodextrins include white dextrin which has heretofore been used generally for foods and pharmaceuticals. White dextrin contains up to 30% of indigestible component and up to 3% of dietary fiber, is about 3.9 kcal/g in both caloric values 1 and 2, and is therefore unusable for foods. Further when containing at least 30% of indigestible component and at least 12% of dietary fiber and having caloric values 1 and 2 of up to 3 kcal/g, such dextrin tastes stimulating and can not be used therefore.

The pyrodextrin for use in the present invention is prepared by adding an aqueous solution of hydrochloric acid, about 1% in concentration, to starch in an amount of 3 to 10% based on the starch, and heating the starch. Since the aqueous acid solution is added before the heat treatment, the starch and the acid are uniformly mixed together by being agitated and aged in a mixer, and the mixture is then heated at 150° to 200° C. for 10 to 120 minutes, preferably for 15 to 60 minutes, unlike the heating condition for preparing conventional pyrodextrins (white dextrin and yellow dextrin). If the reaction temperature is higher, the resulting product will contain increased amount of indigestible component and dietary fiber and have a lower caloric value, whereas increased amount of colored substance will be formed as the temperature rises from about 180° C., so that the temperature is preferably 150° to 180° C.

Since the reaction can be conducted at a high temperature within a shortened period of time by suitably selecting the heater to be used, the mixture can be heat-treated efficiently using an apparatus capable of effecting a uniform reaction. Further because the starch is reacted in the form of powder, there arises a need to alter the heating condition for mass production, so that it is desirable to suitably vary the heating condition by checking the quality of the product as treated.

Next, the pyrodextrin is dissolved in water to a concentration of 20 to 45% and then hydrolyzed with alpha-amylase and thereafter with glucoamylase. Useful alpha-amylases are those commercially available, among which TERMAMYL (heat-resistant alpha-amylase produced by *Bacillus licheniformis* and manufactured by NOVO Industry Co., Ltd.) is most desirable.

Since the pyrodextrin solution has been made acidic with the acid added before the heat treatment, the solution must be adjusted to an optimum pH value for the amylase to be used, with any of common alkalis. Sodium hydroxide is commercially available in the form of a solution and is therefore most advantageous to use. The preferred pH is 5.5 to 6.5. If the value is lower than this range, a reduced reaction velocity will result, whereas higher pH values entail pronounced coloration. After the adjustment of pH, alpha-amylase is added to the solution usually in an amount of about 0.05 to about 0.2%.

The reaction temperature need not to be as high as that is used for the preparation of maltodextrin. Since high temperature rather results in promoted coloration, the temperature is preferably 80° to 90° C. Satisfactory results can be achieved by conducting the reaction usually for about 1 hour.

The reaction mixture is subsequently hydrolyzed with glucoamylase. Any of commercial glucoamylase is useful for this purpose. Glucoamylase generally contains a small amount of alpha-amylase, so that glucoamylase, if singly used, exhibits the effect to be produced by the conjoint use of alpha-amylase and glucoamylase. However, when the amount of alpha-amylase contained is lesser, the effect achieved is slightly smaller than is contemplated by the invention. The most preferred result can be achieved by using alpha-amylase and glucoamylase in combination. The pH preferable for the activity of glucoamylase is 4.0 to 6.0. Like alpha-amylase, glucoamylase is used in an amount of about 0.05 to about 0.2%. The reaction is conducted at a temperature of about 55° to about 60° C. usually for 24 to 48 hours.

The amount of each of the amylases to be used is not limited to the foregoing range but may be used in an amount equivalent thereto in accordance with the activity of the amylase. The reaction time is controllable as desired by varying the amount.

The hydrolyzate obtained by hydrolyzing pyrodextrin with alpha-amylase may be autoclaved at 115° to 135° C., then reacted with alpha-amylase again and thereafter with glucoamylase, whereby the hydrolyzate can be filtered at a higher rate for refining.

The hydrolyzate resulting from the reaction with glucoamylase is lowered in pH to about 3.5, then heated to about 80° C., and thereafter decolorized with activated carbon, filtered, and desalted and decolorized with ion exchange resin in usual manner. The hydrolyzate is subsequently concentrated to a concentration of about 50% and thereafter subjected to continuous ion exchange resin chromatography to separate off the glucose formed. For this procedure, commercial strongly acidic cation exchange resins are usable.

Examples of such resins which are desirable are AMBERLITE IR-116,IR-118, IR120-B, XT-1022E and XT-471F (brand names for products of Japan Organo Co., Ltd.), DIAION 2K-1B, SKK-102, SK-104, SK-106,SK-110, SK-112, SK-116 and FR-01 (brand names for products of Mitsubishi Chemical Industries, Ltd.), and XFS—43281.00, —43280.00, —43279.00 and —43278.00 (brand names for products of Dow Chemical Japan).

It is desirable to use these resins usually as combined with an alkali metal or alkaline earth metal. To render the indigestible fraction efficiently separable from the glucose fraction, it is desirable to pass the hydrolyzate at a flow rate as adjusted to the resin used. The flow rate, SV, is 0.1 to 0.6, preferably 0.2 to 0.4. If the flow rate is outside this range, the operation efficiency or separation efficiency tends to become lower. The hydrolyzate is passed through the column at a temperature of 20° to 70° C., preferably 50° to 70° C. At lower temperature, inefficient separation will result, and an increase in the viscosity of the liquid is likely to cause trouble to the resin, whereas at higher temperature exceeding the specified range, the liquid is likely to turn brown or become otherwise degraded.

While the separation procedure decreases the glucose content to about 0.5%, the glucose content is adjustable as desired by altering the separation condition. Accordingly, in the case where it is desired to use the glucose as a sweetener, the product can be obtained with an increased glucose content. For example when the hydrolyzate as treated with glucoamylase has a glucose content of 50%, a product with an overall glucose content of about 33% can be obtained by separating off one-half, i.e., 25%, of the glucose from the hydrolyzate.

Further it is possible to separate off, along with glucose, a fraction including oligosaccharides and having a medium molecular weight by the separation procedure to obtain a fraction having an increased dietary fiber content of up to about 85%.

Experimental data will be described below to further clarify the features of the present invention.

EXPERIMENTAL EXAMPLES

1. Method of Determining the Content of Indigestible Component

The content was measured by a modified method according to "The method for determining the indigestible part using HPLC" (Journal of Japanese Society of Starch Science, Vol. 37, No. 2, p. 107, 1990) as will be described below.

One gram of a sample was accurately weighed out, and 50 ml of 0.05M phosphate buffer (pH 6.0) was added to the sample, followed by addition of 0.1 ml of Termamyl (alpha-amylase, product of NOVO Industry Co., Ltd.) and reacted at 95° C. for 30 minutes. The reaction mixture was cooled and adjusted to a pH of 4.5. A 0.1 ml quantity of amylo-glycosidase (product of Sigma) was added to and reacted with the mixture at 60° C. for 30 minutes, followed by heating to 90° C. To complete the reaction.

After completion of the reaction, the reaction solution is filled up to 100 ml with water and subjected to the determination of the content of glucose present therein by the pyranose-oxidase method and thus the content of the indigestible components (%) is calculated from the resulting glucose content (B) and that of the sample (A), separately determined in the same manner, prior to the reaction according to the following relation:

The content of indigestible components (% by weight)

$$= [1 - A - (B - A) \times 0.9] \times 100$$

wherein A is glucose content (g) after the reaction.

2. Method of Quantitatively Determining Glycosidic Linkages

A sample was methylated by a modified method of Hakomori's methylation method (S. Hakomori, J. Brioche., 55, 205 (1964)) described below, followed by hydrolysis and thereafter by gas chromatography to quantitatively determine the glycosidic linkages composing the sample.

(1) Methylation

A dehydrated sample (100 to 200 μg) is placed into a test tube (15 mm diam. × 100 mm) with a screw cap and dissolved by addition of 0.3 ml of DMSO. To the solution is added 20 mg of NaH, immediately followed by addition of 0.1 ml of methyl iodide. The mixture is stirred by a touch mixer for 6 minutes and then cooled in ice water, and 2 ml of water is added to the mixture. The mixture is fully shaken with addition of 2 ml of chloroform. The upper layer (aqueous layer) is collected with a pipette and discarded. The remaining layer is similarly washed with addition of 2 ml of water. This procedure is repeated 6 times. Cotton is placed on the bottom of a Pasteur pipette, anhydrous sodium sulfate is placed into the pipette to form a 4- to 5-cm-thick layer, and the solution is passed through the layer for dehydration and then washed with chloroform. Subsequently, the solution is concentrated to dryness in a rotary evaporator.

(2) Hydrolysis

With addition of 0.5 ml of trifluoroacetic acid, the methylated product is hydrolyzed at 100° C. for 4 hours, and the hydrolyzate is concentrated to dryness at 60° C. in a rotary evaporator.

(3) Reduction

The hydrolyzate is dissolved in 0.5 ml of water, and the solution is allowed to stand at room temperature for 2 hours with addition of 10 mg of sodium borohydride. Several drops of acetic acid are added to the mixture until the mixture ceases foaming to terminate the reaction. The mixture is then dried at room temperature and further dried at room temperature with addition of 1 ml of methanol to remove the boric acid formed. This procedure is repeated 6 times.

(4) Acetylation

With addition of 0.5 ml of acetic anhydride, the reduced product is heated at 100° C. for 4 hours and thereby acetylated. With addition of 1 ml of toluene, the product is concentrated to dryness in a rotary evaporator.

(5) Desalting

The acetylated product is dissolved in 1 ml of chloroform, the solution is shaken with addition of 1 ml of water, and the aqueous layer is discarded. After repeating this procedure 5 times, the chloroform is evaporated off from the resulting layer by a rotary evaporator.

(6) Dissolving

The desalted product is dissolved in 0.5 ml of chloroform and subjected to gas chromatography.

(7) Conditions for gas chromatography

Column: DB-1 fused silica capillary column 60 m×0.255 m×I.D., 0.1 μm film
Column temperature: 50° C. for 1 minute, elevation of temperature at a rate of 10° C. min to a constant temperature of 280° C.
Temp. of sample vaporizing chamber: 300° C.
Detection temp.: 300° C.
Flow rate: 2.5 ml/min, helium
Detecting unit: flame ionization detector 3. Method of Determining MN and MW The same solution as used for the quantitative determination of glucose is passed through a column of ion exchange resin of the mixed bed type at SV of 1.0 for desalting, and the effluent is concentrated to a concentration of 5% using a rotary evaporator to obtain a sample. A 20-μl protion of the sample is subjected to liquid chromatography under the following conditions.
Column: Shodex Ionpak S-802.S-804.S-805.S-806
Eluent: 1 ml/min of water
Column pressure: 40 kg/cm²
Column temp.: 60° C.
Detector: RI
Data processor: Hitachi Model D-2000 GPC data processor
Standard sample: glucose, pullulan (with known molecular weight)

MN and MW are calculated from the following equations based on the result of chromatography.

$$MN = \frac{\Sigma Hi}{\Sigma(Hi \div Mi)} \times QF$$

$$MW = \frac{\Sigma(Hi \times Mi)}{\Sigma Hi} \times QF$$

where
Hi: height of peak
Mi: molecular weight of pullulan
QF: Q factor (Mark-Houwink Coefficient)

4. Method of Quantitatively Determining Glucose

One gram of sample is accurately weighed out, placed into a 100-ml measuring flask and diluted to 100 ml with distilled water. This solution is used for the quantitative determination of glucose by the pyranose oxidase (Determiner GL-E, product of Kyowa Medic Co., Ltd.) method.

5. Method of Quantitatively Determining Dietary Fiber Content

Dietary fibers are quantitatively determined by the following Prosky method (No. 985.29, Total Dietary Fiber in Foods, "Official Methods of Analysis", AOAC, 15th Ed., 1990, P. 1105–1106, No. 985.29, Total Dietary Fiber in Foods).

6. Method of Measuring Caloric Value 1

According to the following method titled "Measurement of Physiological Combustion Heat of Food for Specified Health Use Containing Water-Soluble Low Calorie Sugars" which is notified by the Ministry of Health and Welfare of Japan.

6-1. Reagents and Others (a) Somogyi Reagent 90 g of Potassium sodium tartrate and 225 g of sodium tertiary phosphate ($Na_s PO_4 \cdot 12H_2O$) is dissolved in 700 ml of distilled water, and 30 g of copper sulfate ($CuSO_4 \cdot 5H_2O$) and 3.5 g of potassium iodate ($KIO_3$) are added to the solution. The resulting solution is diluted to 1000 ml with distilled water.

(b) Lawry Reagents

Solution A: mixture of 1% copper sulfate ($CuSO_4 \cdot 5H_2O$) solution and 2.2% potassium sodium tartrate solution at a ratio of 1:1
Solution B: mixture of phenol reagent and distilled water at a ratio of 1:0.8

(c) Sugar Alcohol Measuring Kit

F-kit: F-kit D-sorbitol/xylitol, product of Boehringer Mannhelm Yamanouchi Pharmaceutical Co., Ltd.

(d) Diastase Solution

2% solution of diastase (Japanese Pharmacopoeia).

(e) Hydroxylamine Pyridine Solution

Solution of 100 mg of hydroxylamine in 10 ml of pyridine.

(f) Condition for Gas Chromatogrphy

FID gas chromatograph, 5% SE30 chromosorb W, glass or stainless steel column measuring 3 to 4 mm inside diameter and 2 m in length, column temperature 185° C., carrier gas 80 ml/min.

6-2. Determination of Total Water-Soluble Reducing Sugar

(a) Preparation of Test Solution

Oligosaccharides are thoroughly extracted from the sample using water or 89% ethanol when the sample contains only oligosaccharides or using 80% ethanol when the sample contains starch and like polysaccharides. The extract is concentrated under reduced pressure (at not higher than 60° C.), the residue completely dissolved in a small amount of 50 mM maleic acid-Na buffer (pH 6.0), and the solution adjusted to a glucose concentration about 500 mg %.

(b) Procedure

To 1 part of the test solution is added 2 parts 1N hydrochloric acid, and the mixture is heated in a boiling water bath at 100° C. for 20 hours. Then the content of the reducing sugar of the resulting solution is determined by the Somogy's method, and pentose and hexose alcohols therein by gas chromatography or F-kit. The combined amount of carbohyrates determined is taken as the amount of total water-soluble saccharides (A).

(c) Somogyi's Method 2.5 ml of somogyi solution is added to 7.5 ml of test solution (1 to 10 mg, calculated as reducing sugar), and the mixture is heated at 100° C. for 10 minutes, cooled and then thoroughly mixed with 2 ml of 2.5% of potassium iodide (KI) solution and 3 ml of 2N sulfuric acid. The mixture is titrated with 1/40N sodium thiosulfate ($Na_2SO_3 \cdot 5H_2O$). Glucose is used as a standard saccharide. The sugar content of the test solution is determined from the titration value obtained.

(d) Determination of Sugar Alcohol

The test solution hydrolyzed for the determination of total water-soluble sugar is suitable diluted and used to measure the amounts of sorbitol and xylitol by F-kit.

In case the solution contains pentose or hexose alcohol other than sorbitol and xylitol, gas chromatography is used. The test solution hydrolyzed for the determination of total water-soluble sugar is concentrated under reduced pressure at a temperature of up to 60° C.; ethanol is added to the concentrate so as to give a final concentration of at least 80%, and the mixture is heated in a boiling water bath for 30 minutes for extraction. The extract obtained is concentrated under reduced pressure at no higher than 60° C. To the concentrate is added 80% ethanol to obtain a predetermined amount of solution. A 5 ml portion of this solution is collected, from which the solvent is completely removed under reduced pressure. The residue is dissolved in 1 ml of pyridine; 1 ml of hydroxylamine pyridine solution is added to the solution, and the mixture is allowed to stand for 5 minutes and thereafter distilled under reduced pressure to remove the solvent. With the addition of 1 ml of benzene, the residue is treated under reduced pressure to completely remove water, and the resulting residue is dissolved with 2 ml of pyridine. To the solution are added 0.2 ml of hexamethyldisilane and 0.1 ml of trimethylsilane, and the mixture is allowed to stand at room temperature for at least 15 minutes, thereafter adjusted to a predetermined amount with pyridine and subjected to gas chromatography to quantitatively determine sugar alcohol by the absolute calibration curve method.

6-3. Determination of Insoluble Starch

As to samples containing starch, the sample used corresponds to 2.5 to 3.0 mg dry weight resulting residue from extraction with 80% ethanol in the same manner as the extraction of total water-soluble sugar. The residue is dispersed in 200 ml of water, and the dispersion is heated in a boiling water bath for 15 minutes while being continuously stirred, followed by cooling to 55° C. and addition of 10 ml of diastase solution. The resulting mixture is allowed to stand at 55° C. for 1 hour, then boiled for several minutes and thereafter cooled to 55° C. again, followed by addition of 10 ml of diastase solution, continuous stirring and standing for 1 hour. When the substance remaining in the resulting reaction mixture is found positive by iodine-starch reaction, diastase solution is added to the mixture once again for further digestion. If the solution as treated with diastase proves negative when checked by iodine-starch reaction, the solution is diluted to 250 ml with distilled water, then filtered with filter paper. Hydrochloric acid is added to the filtrate to a concentration of 2.5%, and the mixture is heated in a boiling water bath for 2.5 hours, cooled, thereafter neutralized with 10% sodium hydroxide solution and filtered. The filtrate is suitably diluted and used for the determination of glucose by the Somogyi's method. The amount of glucose thus determined is multiplied by 0.9 to obtain a value which is the amount of starch (A').

6-4 Determination of Sugars Digested and Absorbed by the Small Intestine

(a) Determination of Enzyme-Digested Sugars

1) Preparation of solution of commercial rat small intestine acetone powder

Rat small intestine acetone powder, product of Sigma, is put into suspension with addition of physiological saline (0.9% NaCl). The suspension is urtrasonic treated (60 seconds, three times) and thereafter centrifuged (3000 r.p.m., 30 minutes) to obtain a supernatant serving as an enzyme solution. The protein content of the enzyme solution is determined by the Lowry's method. The enzyme activity is adjusted to at least about 0.1 mg/mg protein/hour in terms of sucrose hydrolysis ability.

2) Digestion test with rat small intestine acetone powder

The sample to be used is the same extract as is obtained with use of 80% ethanol or water for the determination of total water-soluble sugar. The extract is concentrated and then diluted with 50 mM maleic acid-Na buffer (pH 6.0) to a sugar concentration of 1 to 4%. A 1.0 ml portion of the solution is admixed with 1.0 ml of the enzyme solution and is reacted therewith at 37° C. for 1 hour. The reaction mixture is heated in a boiling water bath for 10 minutes for inactivation and centrifuged (3000 r.p.m., 30 minutes) to obtain a supernatant. The reducing sugar content of the supernatant is determined by the Somogyi method, and the sugar alcohol content thereof by F-kit or gas chromatography. The sum of these contents is taken as the amount of enzyme-digested absorbable sugar. The contents determined are to include the reducing sugar and sugar alcohol which are originally present in the sample. The decomposition rate is the amount of digested absorbable sugar divided by the amount of total water-soluble sugar and multiplied by 100. As a control test, the same procedure as above is repeated for sucrose or maltose in the same amount as the total water-soluble sugar amount. When sucrose is used for the control test, the decomposition rate is to be at least 20%. The ratio of the decomposition rate obtained for sucrose or maltose to the decomposition rate obtained for the sugar determined is taken as the small intestine digestion absorption ratio; this ratio multiplied by the total water-soluble reducing sugar amount as the amount of total digested absorbable reducing sugar (B), and the amount of total digested absorbable sugar alcohol (C).

Which of sucrose and maltose is to be used as the control sugar is determined by the following method. Maltose in one-half the amount of the sugar determined is used as a substrate for a digestion test under the same condition as used for the digestion test with the rat small intestine acetone powder. If the amount of glucose then produced on digestion is up to 10 times the sum of the sugar and sugar alcohol resulting from the digestion test for the sugar determined, maltose is used as the control sugar. If the amount of glucose is larger than 10 times, sucrose is used.

3) Quantitive determination of protein

A 0.3 ml of 1N sodium hydroxide is added to 0.1 ml of sample (containing 20 to 100 μg of protein), and the mixture is allowed to stand for at least 15 minutes. 3 ml of solution A is then added to the mixture, followed by standing at room temperature for 10 minutes. Subsequently, 0.3 ml of solution B is added to the mixture, and 30 minutes thereafter, the mixture is checked for light absorbancy at 750 nm. Bovine serum albumin is used as a standard protein.

6-5 Equation for Calculating Physiological Combustion Heat

The amount of physiological combustion heat is the sum of amounts of effective energy due to digestion and absorption, and fermentation and absorption. Accordingly, the amount of physiological combustion heat is given by the following equation.

Amount of physiological combustion heat (kcal/g) =(starch A')×4+(amount of total digested absorbable reducing sugar (B))×4+(amount of total digested absorbable sugar alcohol (C))×2.8+((total water-soluble sugar A)−(amount of total digested absorbable reducing sugar (B)+amount of total digested absorbable sugar alcohol (C))×0.5$^{(1)}$×1.9$^{(1)}$ Fermentable ratio of indigestible dextrin in the large intestine.

7. Method of Measuring Caloric Value-2

The effective caloric value of a sample is calculated as the sum of the caloric value-2 resulting from digestion and absorption by the digestive system up to the upper digestive tract, and the caloric value resulting from intestinal fermentation after arrival of the sample at the large intestine.

TEST 1

Measurement of Caloric Value Resulting From Digestion and Absorption by the Upper Digestive Tract up to the Small Intestine The sample is dissolved in 45 mM (bis)Tris buffer (pH 6.0) containing 0.9 mM calcium chloride to obtain a 4.55% solution, to which 160 U/g of human saliva alpha-amylase (SIGMA Type IX-A) is added, followed by a reaction at 37° C. for 30 minutes. After deactivating the enzyme, the reaction mixture is desalted with an ion exchange resin and adjusted to a concentration of 1.1%. The aqueous solution (4 ml) is then added to 2 ml of 50 mM hydrochloric acid-potassium chloride buffer (pH 2.0), and the mixture is maintained at 37° C. for 100 minutes, followed by desalting with an ion exchange resin. To the desalted solution is added 45 mM (bis)Tris buffer (pH 6.0) containing 0.9 mM calcium chloride to adjust the solution to a concentration of 0.45%. To the solution is added 400 U/g of swine pancreatic amylase (product of Boehringer Mannheim Yamanouchi Co., Ltd.), followed by a reaction at 37° C. for 6 hours. The enzyme is then deactivated, and the reaction mixture is thereafter desalted with an ion exchange resin, concentrated and lyophilized.

The powdery sample thus obtained is dissolved in 45 mM sodium maleate buffer (pH 6.6) to prepare a 0.45% solution, with which 86 U/g of rat small intestine mucous membrane enzyme (product of SIGMA) is reacted at 37° C. for 3 hours. The amount of glucose produced is measured by the pyranose oxidase method. The caloric value to be produced by digestion and absorption is calculated from the following equation.

$$\text{Caloric value} = \frac{\text{Amount of glucose produced (\%)} \times 4 \text{ kcal/g}}{100}$$

Test 2

Determination of Caloric Value Resulting from Intestinal Fermentation

The caloric value of the fraction reaching the large intestine was determined by the growth curve method using rats as described below.

TABLE 1

| Component | Proportion (%) |
|---|---|
| Corn starch | 42.7 |
| Casein | 40.0 |
| Fiber | 2.0 |
| Mineral mixture | 10.0 |
| Vitamin mixture | 0.8 |
| DL-methionine | 0.3 |
| Choline bitartrate | 0.2 |
| Vegetable oil | 5.0 |

Rats were preliminarily raised for 5 days to adapt them to the laboratory environment and to the basal diet shown in Table 1, then checked for body weight and health and divided into groups (10 rats in each group). The average initial body weight of all the test groups was 79.6 to 80.8 g. The body weight variations of the groups were in the range 9 to 16 g. The caloric value of all the test components and basal diet was measured by a bomb calorimeter.

TABLE 2

| No. | Basic diet (g) | Glucose (g) | Sample (g) | Total amount (g) | Caloric value (Kcal) |
|---|---|---|---|---|---|
| 1 | 5.4 | — | — | 5.4 | 22.7 |
| 2 | 5.4 | 0.5 | — | 5.9 | 24.7 |
| 3 | 5.4 | 1.0 | — | 6.4 | 26.7 |
| 4 | 5.4 | 2.0 | — | 7.4 | 30.7 |
| 5 | 5.4 | 4.0 | — | 9.4 | 38.7 |
| 6 | 5.4 | — | 0.5 | 5.9 | 24.7 |
| 7 | 5.4 | — | 1.0 | 6.4 | 26.7 |
| 8 | 5.4 | — | 2.0 | 7.4 | 30.7 |

TABLE 2-continued

| No. | Basic diet (g) | Glucose (g) | Sample (g) | Total amount (g) | Caloric value (Kcal) |
|---|---|---|---|---|---|
| 9 | 5.4 | — | 4.0 | 9.4 | 38.7 |

After grouping, the rats were placed into individual steel cages and fed according to the experimental schedule listed in Table 2. The basal diet was given to all the rats in an amount of 5.4 g/rat/kg (22.7 kcal/rat/day). For the test groups, glucose or the above sample was added in an amount of 0.5, 1.0, 2.0 or 4.0 g to the basal diet. The amount of glucose or sample added was about 2, 4, 8 or 16 kcal/rat/day in terms of caloric value. The amount of ingestion was measured daily, and the gain in the body weight was measured on the 0th, 5th, 10th and 15th days. The rats were checked generally every day by observation. Table 3 shows the results.

TABLE 3

| No. | Body weight Initial g | Body weight Final g | Gain g/14 day | Consumed calories KCal/day | Calories needed for 1 g gain |
|---|---|---|---|---|---|
| 1 | 79.2 | 74.4 | −4.8 | 23.2 | — |
| 2 | 79.9 | 78.9 | −1.0 | 24.8 | — |
| 3 | 79.4 | 85.5 | 6.1 | 26.2 | 0.017 |
| 4 | 79.5 | 89.9 | 10.4 | 27.6 | 0.027 |
| 5 | 79.6 | 96.2 | 16.6 | 28.9 | 0.041 |
| 6 | 78.8 | 76.7 | −2.1 | 24.2 | — |
| 7 | 80.3 | 78.4 | −1.9 | 26.9 | — |
| 8 | 79.4 | 82.2 | 2.8 | 28.3 | 0.007 |
| 9 | 79.4 | 86.5 | 7.1 | 29.6 | 0.017 |

With reference to Table 3, the caloric value determined by the animal experiment is:

$(0.007 \div 0.027 \times 4 + 0.017 \div 0.041 \times 4) \div 2 = 1.35$ kcal/g

From Test 1, the caloric value resulting from the digestion and absorption of the sample by the upper digestive tract is:

$$\frac{9.8 \times 4 \text{ kcal/g}}{100} = 0.39 \text{ kcal/g}$$

Accordingly, the caloric value resulting from intestinal fermentation is:

$1.35 - 0.39 = 0.96$ kcal/g

From this data, the caloric value produced by the intestinal fermentation of the dextrin is:

$0.96 \div 0.912$ (proportion reaching the large intestine) $= 1.1$ kcal/g = about 1 kcal/g Thus, according to the methods of Test 1 and Test 2, the caloric value-2 was calculated from the following equation.

$$\text{Caloric value (kcal/g)} = \frac{\text{Glucose produced (\%)} \times 4}{100} + \frac{(100 - \text{glucose produced (\%)}) \times 1}{100} = 1 + \frac{3 \times \text{glucose produced (\%)}}{100}$$

Experimental Example 1

To 15 kg of commercial potato starch was sprayed 1125 ml of a 1% hydrochloric acid solution, and the starch was treated in a mixer to prepare a uniform mixture. The mixture was placed into an aluminum vat, predried in a dryer at 120° C. for 1 hour and then heat-treated at 165° C. for 180 minutes. During the heat treatment, 2 kg portions of the mixture were collected 15 minutes, 30 minutes, 60 minutes, 120 minutes and 180 minutes after the start of the treatment to obtain six samples. The samples were analyzed to determine the contents of glucose, various glycosidic linkages, indigestible component and dietary fiber, caloric value 1, caloric value 2, MN and MW. Detected by this procedure were a glucose residue at each nonreducing end, glucose residues having a 1→4 linkage, glucose residues having a 1→6 linkage, glucose residues having a 1→3 linkage, glucose residues each having both 1→4 linkage and 1→6 linkage, glucose residues each having both 1→3 linkage and 1→4 linkage, glucose residue each having both 1→2 linkage and 1→4 linkage, and glucose residues having other linkages. The value of glucose determined by the method used included the content of glucose residues at the nonreducing ends, so that the content of glucose residues given is this value minus the content of glucose. Table 4 shows the values obtained.

The method of quantitative determination is complex and involves errors which are usually about ±5% and are invariably ±2% if minimum.

TABLE 4

| Item | Heating time (min.) 15 | 30 | 60 | 120 | 180 |
|---|---|---|---|---|---|
| Contents of linkage (%) | | | | | |
| non-reduced end | 10.6 | 12.8 | 15.6 | 17.4 | 14.6 |
| 1→4 | 78.6 | 73.6 | 68.9 | 64.4 | 54.1 |
| 1→6 | 1.7 | 2.7 | 4.3 | 5.7 | 5.4 |
| 1→3 | — | — | — | — | 1.5 |
| 1→4, 1→6 | 6.8 | 7.9 | 9.8 | 10.1 | 8.9 |
| 1→3, 1→4 | 1.0 | 1.3 | — | — | 1.0 |
| 1→2, 1→4 | 1.3 | 1.7 | 1.4 | 2.4 | 2.3 |
| others | — | — | — | — | 12.2 |
| Content of indigestible component (%) | 24.4 | 34.3 | 43.5 | 54.9 | 60.9 |
| Content of dietary fiber (%) | 5.2 | 8.6 | 11.2 | 14.6 | 15.2 |
| Caloric value 1 (kcal/g) | 3.42 | 3.18 | 2.96 | 2.69 | 2.55 |
| Caloric value 2 (kcal/g) | 3.27 | 2.97 | 2.70 | 2.35 | 2.17 |
| MN | 1789 | 1972 | 1588 | 1452 | 1487 |
| MW × $10^{-3}$ | 683 | 642 | 553 | 551 | 547 |
| MW/MN | 382 | 326 | 348 | 379 | 368 |

With the sample heated for 180 minutes, the prolonged heating presumable broke down the component sugars of starch, so that the results given in Table 4 will be discussed except for this sample. The contents of indigestible component and dietary fiber increase in proportion to the heating time. The caloric values decrease in inverse proportion to the heating time. The contents of glucose residues with various glycosidic linkages, i.e., those having 1→6 glycosidic linkage, those having 1→3 glycosidic linkage, those having both 1→4 and 1→6 glycosidic linkages, those having both 1→2 and 1→4 glycosidic linkages, and those having other linkages, increase in proportion to the heating time. Only the content of residues with 1→4 linkage decreases in inverse proportion to the heating time. The values MN decrease and increase during heating and MW/MN decrease during heating for 30 minutes and increase again in proportion to the heating time after 60 minutes. These variations in the glycosidic linkage contents and average molecular weights with the heating time are novel findings obtained by the experiment for the first time.

Experimental Example 2

2 liters of water was added to 1 kg of each of the six samples of Experimental Example 1 to prepare a solution, which was then adjusted to a pH of 6.0 with 20% sodium hydroxide and hydrolyzed with 0.2 wt. % of alpha-amylase sold under the tradename TERMAMYL 60L, by NOVO Industry Co., Ltd. at 85° C. for 1 hour. The hydrolyzate was cooled to a temperature of 55° C., then adjusted to a pH of 5.5 and hydrolyzed with 0.2 wt. % of glucoamylase (product of Amano Seiyaku Co., Ltd.) for 36 hours, whereupon the resulting hydrolyzate was adjusted to a pH of 3.5 to inactivate the glucoamylase. The hydrolyzate was refined by decolorization with activated carbon, filtration and desalting with an ion exchange resin. The samples thus obtained were analyzed in the same manner as in Experimental Example 1. Table 5 shows the values obtained. The hydrolyzate obtained before the addition of glucoamylase was also checked for MN, MW and MW/MN. Table 6 shows the results.

Table 5 reveals the following distinct features.

The 1→4 glycosidic linkage fraction greatly diminished, but about 10 to about 20% thereof still remained unhydrolyzed. This means that the 1→4 linkage fraction which should have been hydrolyzed almost completely with glucoamylase remained unhydrolyzed in an amount as large as 10 to 20%.

2) No marked hydrolysis occurred in the fractions except in the 1→4 and 1→6 glycosidic linkage fractions. The fact that the caloric values remained almost unincreased indicates that the low-calorie fraction remained almost unhydrolyzed with alpha-amylase and glucoamylase.

3) 1→3 glycosidic linkage increased, however reason is unknown.

4) Suppose one-half of glucose is removed, for example, from the sample prepared by 15 minute heating. This results in an indigestible content of 37.3% and a dietary fiber content of 7.8%.

5) The ratio MW/MN, which is about 10 to about 300, is exceedingly greater than the corresponding value of the prior art which is up to 20.

Table 6 reveals that the hydrolyzates before being hydrolyzed with glucoamylase were as high as about 40 to about 180 in MW/MN.

These result are novel findings obtained by the experiment for the first time.

Experimental Example 3

Each of the six samples of Experimental Example 2 was concentrated to obtain about 1.5 liters of 50% solution. 1 liter portion of the solution was passed, at a solution temperature of 60° C. and at SV 0.25, through a column packed with 10 liters of XFS-43279.00 (product of Dow Chemical Japan), strongly acidic cation exchange resin of the alkali metal type. Subsequently, water was passed through the column to collect an indigestible fraction (as separated off from the glucose

TABLE 5

| Item | Heating time (min.) | | | | |
|---|---|---|---|---|---|
| | 15 | 30 | 60 | 120 | 180 |
| Contents of linkage (%) | | | | | |
| non-reduced end | 8.2 | 11.4 | 13.7 | 15.6 | 17.4 |
| 1→4 | 10.2 | 13.3 | 14.3 | 19.5 | 19.8 |
| 1→6 | 3.3 | 4.3 | 5.5 | 6.2 | 6.3 |
| 1→3 | 4.2 | 3.7 | 4.0 | 3.7 | 5.4 |
| 1→4, 1→6 | 2.3 | 3.8 | 5.0 | 6.5 | 6.7 |
| 1→3, 1→4 | 0.6 | 0.8 | 0.9 | 0.9 | 1.2 |
| 1→2, 1→4 | 0.5 | 0.7 | 1.0 | 1.1 | 1.6 |
| others | 1.5 | 1.0 | 3.1 | 3.2 | 4.3 |
| Content of glucose (%) | 69.2 | 61.0 | 52.5 | 43.3 | 37.3 |
| Content of indigestible component (%) | 24.4 | 30.5 | 39.9 | 51.1 | 55.4 |
| Content of dietary fiber (%) | 5.1 | 8.4 | 10.9 | 14.3 | 14.8 |
| Caloric value 1 (kcal/g) | 3.42 | 3.27 | 3.05 | 2.78 | 2.68 |
| Caloric value 2 (kcal/g) | 3.27 | 3.09 | 2.80 | 2.47 | 2.34 |
| MN | 107 | 144 | 139 | 185 | 148 |
| MW × $10^{-3}$ | 1.47 | 1.42 | 2.09 | 20.2 | 44.3 |
| MW/MN | 13.7 | 9.86 | 15.0 | 109 | 299 |

TABLE 6

| Item | Heating time (min.) | | | | |
|---|---|---|---|---|---|
| | 15 | 30 | 60 | 120 | 180 |
| MN | 784 | 737 | 802 | 890 | 850 |
| MW × $10^{-3}$ | 31.4 | 29.8 | 97.6 | 157 | 136 |
| MW/MN | 40.1 | 40.4 | 122 | 176 | 160 | fraction). The sample thus obtained was analyzed in the same manner as in Experimental Example 1. Table 7 shows the results including average molecular weights, etc. In Table 7, the values were expressed in percentages based on the fraction other than glucose. The content (%) of indigestible component in the fraction other than glucose is a value obtained by subtracting the glucose content (%) from 100, dividing the measured amount of indigestible component by the remainder and multiplying the quotient by 100. Similarly, the content (%) of dietary fiber in the fraction other than glucose is a value obtained by subtracting the glucose content (%) from 100, dividing the measured amount of dietary fiber by the remainder and multiplying the quotient by 100.

Further similarly, the caloric value of the fraction other than glucose is a value obtained by multiplying the glucose content (%) by 4 (caloric value of 1 g of glucose), dividing the product by 100 and subtracting the quotient from the measured caloric value. The theoretical yield is a value obtained by subtracting the glucose content of Table 5 from 100.

TABLE 7

| Item | Heating time (min.) | | | | |
|---|---|---|---|---|---|
| | 15 | 30 | 60 | 120 | 180 |
| Contents of linkage (%) | | | | | |
| non-reduced end | 26.6 | 29.2 | 28.9 | 27.4 | 27.8 |
| 1→4 | 33.1 | 34.1 | 30.1 | 34.5 | 31.6 |
| 1→6 | 10.7 | 11.0 | 11.6 | 10.9 | 10.0 |
| 1→3 | 13.6 | 9.5 | 8.4 | 6.5 | 8.6 |
| 1→4, 1→6 | 7.5 | 9.7 | 10.5 | 11.5 | 10.7 |
| 1→3, 1→4 | 2.0 | 2.1 | 1.9 | 1.6 | 1.9 |
| 1→2, 1→4 | 1.6 | 1.8 | 2.1 | 1.9 | 2.5 |
| others | 4.9 | 2.6 | 6.5 | 5.7 | 6.9 |
| Content of glucose (%) | 0.6 | 0.7 | 0.8 | 0.7 | 0.5 |
| Content of indigestible component (%) | 83.9 | 85.4 | 88.9 | 94.5 | 92.0 |
| Content of dietary fiber (%) | 17.7 | 23.1 | 24.3 | 26.5 | 24.6 |
| Caloric value 1 (kcal/g) | 2.00 | 1.97 | 1.88 | 1.75 | 1.81 |
| Caloric value 2 (kcal/g) | 1.48 | 1.44 | 1.33 | 1.17 | 1.24 |
| MN | 533 | 678 | 756 | 962 | 896 |
| MW × $10^{-3}$ | 8.26 | 17.6 | 25.8 | 43.8 | 90.4 |
| MW/MN | 15.5 | 26.0 | 34.1 | 45.5 | 101 |
| Theoritical yield (%) | 30.8 | 39.0 | 47.5 | 62.6 | 56.7 |

With reference to Table 7, the content of indigestible component and the caloric values each remain make no difference with the heating time, but the dietary fiber content increases in proportion to the heating time. The theoretical yield, which corresponds to the proportions of indigestible component, dietary fiber and low calorie component, increases in proportion to MN, MW and MW/MN. The table further reveals that the theoretical yield increases to at least about 40% when MW/MN is at least 25. This indicates that the hydrolyzate before the separation of the glucose fraction by the ion exchange resin is high in the contents of indigestible component and dietary fiber and low in caloric values.

(Incidentally, the content of indigestible component in the overall hydrolyzate containing glucose can be readily obtained by subtracting the glucose content (%) from 100, multiplying the corresponding content of Table 7 by the remainder and dividing the product by 100. Similarly, the content of dietary fiber in the overall hydrolyzate containing glucose can be obtained by subtracting the glucose content (%) from 100, multiplying the corresponding content of Table 7 by the remainder and dividing the product by 100. Further the caloric value of the overall hydrolyzate containing glucose can be obtained by multiplying the glucose content (%) by 4, dividing the product by 100 and adding the quotient to the caloric value of Table 7.) The relationship between the important value MN and the different glycosidic linkage fractions was investigated by regression analysis for determining the correlation between variables to obtain equations and correlation coefficients. The correlation analysis was conducted for the five samples except the sample which was obtained by 180 minutes heating and wherein the component sugars appeared to have been broken down, using the amounts of glucose residues having various glycosidic linkages as predictor variables and the MN values as criterion variables. Table 8 shows eight equations and correlation coefficients obtained.

$$Y = A0 + An \cdot Xn$$

Where
- Y: MN of the component other than glucose
- X1: amount (%) of nonreducing end glucose residues
- X2: amount (%) of glucose residues having a 1→4 glycosidic linkage
- X3: amount (%) of glucose residues having a 1→6 glycosidic linkage
- X4: amount (%) of glucose residues having a 1→3 glycosidic linkage
- X5: amount (%) of glucose residues having 1→4 and 1→6 glycosidic linkages
- X6: amount (%) of glucose residues having 1→3 and 1→4 glycosidic linkages
- X7: amount (%) of glucose residues having 1→2 and 1→4 glycosidic linkages
- X8: amount (%) of glucose residues having other glycosidic linkages

TABLE 8

| No. | equation | correlation coefficient |
|---|---|---|
| 1 | Y = 220 + 19.466.X1 | 0.120 |
| 2 | Y = 766 − 0.031.X2 | 0.000 |
| 3 | Y = 1469 − 64.944.X3 | 0.219 |
| 4 | Y = 1321 − 59.643.X4 | 0.915 |
| 5 | Y = −293 + 106.004.X5 | 0.945 |
| 6 | Y = 2118 − 712.134.X6 | 0.778 |
| 7 | Y = 109 + 331.412.X7 | 0.662 |
| 8 | Y = 488 + 52.145.X8 | 0.518 |

Consequently, MN was found to have the highest correlation with X5 (amount of glucose residues having both 1→4 and 1→6 glycosidic linkages) all the contents of eight kinds of glycosidic linkages as represented by the equation of Table 8, No. 5 (correlation coefficient: 0.945). This equation (hereinafter referred to as "Equation 1") reveals the novel fact that the smaller the amount of glucose residue having both 1→4 and 1→6 glycosidic linkages, the greater the MN, that is, the higher the content of indigestible component and dietary fiber the lower the caloric value.

Experimental Example 4

To 300 kg of commercial potato starch was added 5.8 liters of 3% hydrochloric acid, and the starch was treated in the same manner as in Experimental Example 1 except that the starch was heat-treated at 180° C. for 30 minutes, followed by the same procedures as in Experimental Examples 2 and 3 to obtain a sample. The sample was analyzed in the same manner as in Experimental Example 3.

Experimental Example 5

To 300 kg of commercial potato starch was added 9 liters of 2% hydrochloric acid, and the starch was treated in the same manner as in Experimental Example 1 except that the starch was heat-treated at 150° C. for 60 minutes, followed by the same procedure as in Experimental Example 4 to obtain a sample, which was then analyzed in the same manner as in Experimental Example 3. Table 9 shows the analytical results obtained in Experimental Examples 4 and 5 and including MN values which are given in comparison with those calculated from Equation 1.

TABLE 9

| Item | Example 4 | Example 5 |
|---|---|---|
| Contents of linkage (%) | | |
| non-reduced end | 29.1 | 27.7 |
| 1→4 | 34.5 | 33.1 |
| 1→6 | 10.4 | 11.2 |
| 1→3 | 7.2 | 10.9 |
| 1→4, 1→6 | 10.2 | 10.0 |
| 1→3, 1→4 | 1.8 | 1.9 |
| 1→2, 1→4 | 2.1 | 1.8 |
| others | 4.7 | 3.4 |
| content of glucose (%) | 0.8 | 0.6 |
| content of indigestible component (%) | 86.2 | 93.5 |
| content of dietary fiber (%) | 22.4 | 25.8 |
| caloric value 1 (kcal/g) | 1.95 | 1.77 |
| caloric value 2 (kcal/g) | 1.41 | 1.20 |
| MN measured value | 954 | 704 |
| MN calculated value | 788 | 767 |
| Difference between calculated value and measurement (%) | −17.4 | +8.9 |

The Variation of the calculated value from the measured value was −17.4% in Experimental Example 4 and ÷8.9% in Experimental Example 5.

Experimental Example 6

The sample of Experimental Example 2 obtained by 30 minutes heating was concentrated to prepare about 1.5 liters of 50% solution. The solution (100 ml) was passed through a column packed with 160 ml of Ionpack S-2006 (product of Showa Denko Co., Ltd.) which is a styrene-divinylbenzene copolymer of the sodium type having its molecular weight corrected with pullulan, at a column temperature of 60° C. and at SV of 0.25. Subsequently, water was passed through the column to collect four fractions (as separated from a fraction of glucose and oligosaccharides) o The four fractions were checked for the content of dietary fiber. Table 10 shows the result.

TABLE 10

| | Sample No. | | | |
|---|---|---|---|---|
| | 1 | 2 | 3 | 4 |
| content of dietary fiber (%) | 85.8 | 43.7 | 32.5 | 14.3 |

The dietary fiber content, which was 23.1% in Table 7, increased to a maximum of 85.8% as shown in Table 10.

Comparative Example 1

A sample was prepared in the same manner as in Experimental Example 4 with the exception of adding 22.5 liters of 1% hydrochloric acid to 300 kg of commercial corn starch, treating the mixture in the same manner as in Experimental Example 1 and heating the mixture at 165° C. for 1 hour. The sample was analyzed in the same manner as in Experimental Example 4. MN was calculated from Equation 1.

Comparative Example 2

A sample was prepared in the same manner as in Experimental Example 4 with the exception of adding 22.5 liters of 1% hydrochloric acid to 300 kg of commercial sweet potato starch, treating the mixture in the same manner as in Experimental Example 1 and heating the mixture at 165°0 C. for 1 hour. The sample was analyzed in the same manner as in Experimental Example 4, and MN was calculated from Equation 1.

Table 11 shows the results obtained in Comparative Examples 1 and 2.

TABLE 11

| Item | Comp. Example 1 | Comp. Example 2 |
|---|---|---|
| Contents of linkage (%) | | |
| non-reduced end | 21.2 | 23.9 |
| 1→4 | 26.3 | 25.0 |
| 1→6 | 12.0 | 13.9 |
| 1→3 | 11.2 | 10.8 |
| 1→4, 1→6 | 10.0 | 9.5 |
| 1→3, 1→4 | 1.7 | 1.5 |
| 1→2, 1→4 | 3.7 | 2.9 |
| others | 13.9 | 12.5 |
| content of glucose (%) | 0.8 | 1.2 |
| content of indigestible component (%) | 97.4 | 94.3 |
| content of dietary fiber (%) | 41.7 | 32.4 |
| caloric value 1 (kcal/g) | 1.69 | 1.76 |
| caloric value 2 (kcal/g) | 1.09 | 1.17 |
| MN measured value | 1207 | 1119 |
| MN calculated value | 767 | 714 |
| Difference between calculated value and measurement (%) | −36.5 | −36.2 |

With reference to Table 11, the difference of the calculated MN value from the measured value is −36.5% in Comparative Example 1 and −36.2% in Comparative Example 2, hence a great difference. This indicates that the correlation between the content of glucose residue having both 1→4 and 1→6 glycosidic linkages and MN as represented by Equation is absent therebetween, showing that different starches serving as materials produce products which are greatly different in structure even if heat-treated under the same condition.

Experimental Example 7

The eight pyrodextrin samples obtained in Experimental Examples 1, 4 and 5 were checked for the degree of coloration by measuring the whiteness of the samples relative to the whiteness of magnesium oxide taken as 100%, using photoelectric whiteness meter (product of Kett Co.) and a blue filter. Table 12 shows the results.

TABLE 12

| Ex. | heating temp. (°C.) | heating time (min.) | Whiteness (%) |
|---|---|---|---|
| 1 | 165 | 15 | 63.7 |
| 1 | 165 | 30 | 45.3 |
| 1 | 165 | 60 | 35.3 |
| 1 | 165 | 120 | 34.2 |
| 1 | 165 | 180 | 31.6 |
| 4 | 180 | 30 | 42.2 |
| 5 | 150 | 60 | 41.5 |

Table 12 shows that the whiteness decreases in inverse proportion to the heating time and heating temperature.

Next to check the indigestible dextrin of the invention for physiological activities, the samples of Examples 2 to 4 to be described later were used, which will be referred to as "samples A, B and C" respectively, in Experimental Examples 8 to 14.

Experimental Example 8

Animal experiment

Male rats of Sprague-Dawley strain (6 rats/group) initially weighing about 50 g were accommodated in individual cages placed in a small animal breeding chamber controlled to 23°±2° C., preliminarily raised with a commercial synthetic diet for 1 week, and thereafter fed for 7 days with a basal diet, or the basal diet containing 5% of the sample A, B or C added thereto, or the basal diet containing 5% cellulose (Avicel, product of Sanyo-Kokusaku Pulp Co., Ltd.) with free access to water and the diet. The intake of diet and changes in body weight were recorded daily. On the seventh day, carmine (pigment) was given as admixed with the diet, and the time taken for the carmine to appear in feces was measured as transit time. The animals were thereafter sacrificed with blood taken, and the cecum was removed and checked for the weight thereof, pH of the contents of the cecum and the amount of butyric acid therein. Table 13 shows the average values of results obtained.

TABLE 13

| | Weight of cecum (g) | Contents of cecum (pH) | Amount of butyric acid (mg/cecum) | Excretion time (hr) |
|---|---|---|---|---|
| Basal diet | 1.2 | 8.0 | 4.0 | 13.2 |
| Basal diet + Sample A | 3.5 | 6.3 | 16.9 | 8.8 |
| Basal diet + Sample B | 4.4 | 5.9 | 22.8 | 8.1 |
| Basal diet + Sample C | 3.8 | 5.9 | 21.9 | 8.8 |
| Basal diet + cellulose | 2.5 | 7.6 | 4.3 | 8.2 |

The results listed in Table 13 reveal that the sample A, B or C reached the large intestine while remaining indigested, metabolized to organic acids under the action of enterobacteria and resulted in a lower pH within the intestine. While the ingestion of any of the samples A, B and C shortened the transit time, comparison with the group receiving cellulose, which is effective for improved defecation, indicated that the samples A, B and C were effective. Accordingly, the sample B was further used for clinical tests to substantiate its effect.

Experimental Example 9

Clinical test

The sample B was given at a daily dose of 10 g to ten males in good health during a test period of 2 weeks. During the first and second weeks of the test period, they are given the same meals in same quantities, and the sample was administered after breakfast on Monday through Friday. Feces were collected on every defecation and checked for wet weight, dry weight, moisture content and frequency of defecation. Table 14 shows the results, which reveal that the sample has an effect to increase the overall amount of feces.

TABLE 14

| Test period | Non-ingestion period | Ingestion period |
|---|---|---|
| Wet weight of feces | 556 | 790* |
| Dry weight of feces | 132 | 161* |
| Amount of water in feces | 424 | 629* |
| Water content of feces | 76.3% | 79.6% |
| Frequency of excretion | 4.8 | 6.2* |

Each value listed is mean value, and the mark * indicates a significance level of 5% relative to the non-ingestion period, hence a significant difference.

Experimental Example 10

Clinical test

The sample B was checked for a constipation alleviating effect. The sample was given to 25 volunteers having a tendency toward constipation at a predetermined dose for at least 5 days. Changes resulting from the administration of the sample in defecation were checked with a questionnaire. Scores were assigned to the check items on the questionnaire according to the following criteria to substantiate the effect through a statistical procedure.

(1) Frequency of excretion At least once/day: score 4 Once/day: score 3 Once/two days: score 2 Once/three days: score 1

(2) Amount of excretion Large: score 4 Usual: score 3 Small: score 2 None: score 1

(3) State of feces Bananalike, pasty: score 2 Hard: score 1

(4) Feeling after defecation Complete discharge : score 2 Incomplete discharge : score 1

Table 15 shows the results. The mark * listed indicates a significance level of 5% relative to "before administration," hence a significant difference.

TABLE 15

| | Amount administered | |
|---|---|---|
| | 5 g | 10 g |
| Before administration | 8.04 | 8.15 |
| After administration | 11.25* | 12.72* |

With reference to Table 15, the sample B, when administered at a dose of at least 5 g, resulted in increased scores and was found effective for alleviating constipation.

Experimental Example 11

Animal test

Rats were used for a nutritional experiment to check the samples A, B and C for a serum lipid lowering effect.

Male rats of Sprague-Dawley strain initially weighing about 50 g (3-week-old, provided by CLEA Japan Co.) were preliminarily raised for two weeks on a high-sucrose diet (basal diet) shown in Table 16, and thereafter raised and divided into five groups (10 rats in each group) for 9 weeks, during which the basal diet was given to the first group (control group), and a test diet comprising 95% of the basal diet and 5% of the sample A, B or C admixed therewith was given the second group (sample A group), third group (sample B group) and fourth group (sample C group), with free access to the diet and water.

TABLE 16

| Material | Weight parts |
|---|---|
| Casein | 25 |
| Corn oil | 5 |
| Salt (MM-2) mixture | 4 |
| Vitamin (Harper) mixture | 1 |
| Choline chloride | 0.2 |
| Vitamin E | 0.05 |
| Sucrose | 64.75 |

In the 9th week, the rats were fasted for 4 hours, blood was then taken, and the serum total cholesterol value and neutral fat value thereof were determined by a kit for enzyme method (product of Wako Jun-yaku Co., Ltd.). Table 17 shows the results.

TABLE 17

| | Group | | | |
|---|---|---|---|---|
| Item | 1st | 2nd | 3rd | 4th |
| Weight gain (g/9 weeks) | 297 | 288 | 293 | 296 |
| Diet efficiency | 0.25 | 0.25 | 0.25 | 0.25 |
| Serum total cholesterol (mg/dl) | 125 | 70 | 65 | 86 |
| Serum neutral fat (mg/dl) | 275 | 153 | 112 | 188 |

The results achieved by the test groups are expressed in mean values. The diet efficiency was calculated from Equation 2.

Equation 2

Diet efficiency = weight gain ÷ diet intake

As seen from Table 17, there was no difference between the three sample groups in weight gain and diet efficiency. However, the sample A, B and C groups were apparently lower in serum total cholesterol value and neutral fat value than the control group. The samples A and B were found to be remarkably effective. Accordingly, sample B was further tested clinically.

Experimental Example 12

Clinical test

Sample B (10 g) was dissolved in 100 ml of water, and the solution was orally administered to 10 persons three times a day before every meal for four weeks, during which they observed usual eating habits and were allowed to perform routine work. The persons participating in the test were 34 to 61 years old (53.3 on the average age), 161 to 173 cm tall (166.8 cm on the average) and weighed 54 to 82 kg (65.9 kg on the average). Table 18 shows the results obtained as expressed in the unit of mg/dl.

TABLE 18

| Item | Normal value | Before administration | After administration |
|---|---|---|---|
| Total cholesterol | 120~250 | 235 | 175 |
| HDL-cholesterol | 40~65 | 44 | 47 |
| Neutral fat | 67~172 | 275 | 165 |

Table 18 reveals that the administration of the sample B altered the serum total cholesterol value toward the normal value (120–250 mg/dl). Those who were higher than the normal in this value exhibited a reduction. As similar result was observed also with respect to the neutral fat value. These results substantiate that the sample B has a remarkable effect in improving serum lipid metabolism.

Experimental Example 13

Insulin

An experiment conducted with 36 rats revealed that the blood sugar value of 98.3 mg/dl on average and the insulin secretion of 18.5 $\mu$U/ml on average, when the rats were hungry, increased to the highest levels of 159 mg/dl and 82.4 $\mu$U/ml on average, respectively, 30 minutes after glucose was orally given to the rats in an amount of 1.5 g/kg body weight, and lowered to the respective normal values 120 minutes thereafter. However, addition of the sample B and C to the glucose in an amount of 0.15 g (in a proportion of 1/10 to the amount of glucose) resulted in smaller increases 30 minutes after administration; the average blood sugar value thereby increased and were 163 mg/dl and 164 mg/dl, respectively, and the average value of insulin secretion thereby increased and were 40.2 $\mu$U/ml and 44.5 $\mu$U/ml, respectively. This indicates that the sample B and C significantly suppresses the rise of blood sugar value and insulin secretion due to glucose.

Experimental Example 14

Clinical Test 50 g of glucose, 50 g of glucose and 20 g of the sample B or the sample C were given to 6 males in good health after fasted for 24 hours. Blood sugar value and value of insulin secretion were determined after 30 minutes. Test for each sample were executed 7 days interval and table 19 shows the result obtained.

TABLE 19

| | Blood sugar (mg/dl) | Insulin secretion ($\mu$U/ml) |
|---|---|---|
| Glucose 50 g | 125 | 41.8 |

TABLE 19-continued

| | Blood sugar (mg/dl) | Insulin secretion (μU/ml) |
|---|---|---|
| Glucose 50 g + Sample B 20 g | 126 | 25.8 |
| Glucose 50 g + Sample C 20 g | 133 | 28.1 |

Table 19 reveals the sample B and C has an activity to prevent the increasing of insulin secretion.

Summary of Results of Experimental Data Analysis

To sum up the foregoing results of experimental data analysis, the product of the invention obtained by hydrolyzing pyrodextrin with alpha-amylase and glucoamylase distinctly differs from known pyrodextrins with respect to the following. More specifically stated, the fraction of the present dextrin other than glucose has the following features.

(1) The content of indigestible component is max 94.5%, and the dietary fiber content is max 26.5%. With the fraction of oligosaccharides further removed, the fraction maximally contains 85.8% of dietary fiber and is minimally 1.75 kcal/g in caloric value 1 and 1.17 kcal/g in caloric value 2.

(2) In MN, the fraction is about 500 to about 1000 as compared with conventional pyrodextrins which are at least 1450. The theoretical yield is at least about 39% in the case where MW/MN is at least 25. The contents of indigestible component and dietary fiber increase in proportion to the value MW/MN, and the caloric value decreases in inverse proportion thereto.

(3) In the content of glucose residues having 1→4 glycosidic linkage, the fraction is about 25 to about 30% against about 54% of known pyrodextrins.

(4) In the content of glucose residues having 1→6 glycosidic linkage, the fraction is about 10 to about 11% against about up to 6% of known pyrodextrins.

(5) In the content of glucose residues having 1→3 glycosidic linkage, the fraction is about 7 to about 14% against about up to 2% of known pyrodextrins.

(6) As represented by Equation 1, the content of glucose residues having both 1→4 and 1→6 glycosidic linkages has close correlation with the MN of the fraction. This means that there is close correlation between the content of glucose residues having both 1→4 and 1→6 glycosidic linkages and the proportions of indigestible component and dietary fiber formed.

(7) When at least one-half of digestible glucose is removed from the hydrolyzate to obtain an indigestible fraction, the fraction contains at least 37.3% of indigestible component, 7.8% of dietary fiber and is up to 3.11 kcal/g in caloric value 1 and up to 2.88 kcal/g in caloric value 2.

(8) A starch other than potato starch, i.e., corn starch or sweet potato starch, was treated under the same condition as potato starch. The content of glucose residue having both 1→4 and 1→6 glycosidic linkages and present in the product obtained was substituted in Equation 1 to calculate MN. A great difference of at least about −36% was found between the calculated value and the actual measurement. This indicates that Equation 1 is true only with potato starch specifically.

(9) An increase in the content of indigestible component results in an increased dietary fiber content and a reduced caloric value.

(10) Furthermore, the indigestible dextrin, when ingested, is found effective for improving the internal environment of the intestine and eliminating constipation and diarrhea as by giving a lower pH to the interior of the intestine and increasing the amounts of short chain fatty acids having an intestine conditioning effect.

(11) The dextrin further acts to diminish cholesterol and neutral fats among other serum lipids, consequently preventing arterial sclerosis and hypertension.

(12) Furthermore the dextrin has activity to reduce the insulin secretion.

(13) Because of these effects, the indigestible dextrin of the present invention is very useful as a material for alimentotherapy to accomplish the above purposes.

The above experimental results show that the product of the invention is a novel substance containing exceedingly larger amounts of indigestible component and dietary fiber and having a lower caloric value than conventional pyrodextrins, and greatly different From known pyrodextrins in structure.

The Experimental data further indicates that the whiteness decreases in inverse proportion to the heating time. The decrease in whiteness demonstrates an increase in the amount of colored substance due to the heat treatment. The increase in the amount of colored substance presents difficulty in refining the product before the separation, consequently lowering the efficiency of the ion exchange resin for use in the separation treatment. The whiteness must therefore be at least 30%, preferably at least 40%. Table 12 shows that the heat treatment is to be conducted preferably for not more than 60 minutes when the heating temperature is 150° C., or for not longer than about 45 minutes at 165° C. or for not longer than 30 minutes at 180° C.

Although the progress of the reaction can be controlled by varying the amount of acid to be added to potato starch, use of a greatly increased amount of acid causes corrosion or abrasion to the apparatus, so that the optimum amount of acid to be used is up to 3000 ppm, preferably about 1000 ppm, based on the starch.

EXAMPLES

Examples of the present invention will be given below.

Example 1

Commercial potato starch (2500 kg) was placed into a ribbon mixer, and 188 liters of 1% hydrochloric acid solution was sprayed onto the starch with use of pressurized air while rotating the mixer. The mixture was then passed through a disintegrator to obtain a uniform mixture, which was thereafter aged in the ribbon mixer for 8 hours. The mixture was predried to a moisture content of about 4% by a flash dryer, subsequently continuously charged into a converter of the rotary kiln type and heat-treated at 165° C. for 40 minutes to obtain a pyrodextrin.

Water (4000 liters) was added to the pyrodextrin (2000 kg) to prepare a solution, which was then adjusted to a pH of 6.0 with 20% aqueous solution of sodium hydroxide. With addition of 0.1 wt. % of alpha-amylase (TERMAMYL 60L, product of NOVO Industry Co., Ltd.), the solution was hydrolyzed at 90° C. for 1 hour. The hydrolyzate was then autoclaved at 125° C. for 10 minutes, thereafter discharged into the atmosphere, cooled to a temperature of 57° C., adjusted to a pH of 5.5 and hydrolyzed for 40 hours with 0.1 wt. % of glucoamylase (product of Daiwa Kasei Co., Ltd.) added thereto. The resulting hydrolyzate was adjusted to a pH of 3.6 to inactivate the glucoamylaze. The hydrolyzate was decolorized with activated carbon, filtered, desalted with ion exchange resins and thereafter concentrated to obtain a 50% solution. A 20 liter portion of the solution was passed at 60° C. at SV 0.25 through the column of a continuous chromatographic device packed with 10 liters of XFS-43279.00 (product of Dow Chemical Japan), which is a strongly acidic cation exchange resin of the sodium type. Subsequently, water was passed through the column to separate off a glucose fraction and obtain an indigestible fraction. The fraction was concentrated to concentration of 50% and spray dried to obtain about 4 kg of an indigestible dextrin having a moisture content of 4.1%.

Example 2

Commercial potato starch (2500 kg) was placed into a ribbon mixer, and 125 liters of 2% hydrochloric acid solution was sprayed onto the starch with use of pressurized air while rotating the mixer. The mixture was then passed through a disintegrator to obtain a uniform mixture, which was thereafter aged in the ribbon mixer for 10 hours. The mixture was predried to a moisture content of about 3% by a flash drier, subsequently continuously charged into a converter of the rotary kiln type and heat-treated at 150° C. for 55 minutes to obtain a pyrodextrin.

Water (3000 liters) was added to the pyrodextrin (2000 kg) to prepare a solution, which was then adjusted to a pH 6.0 with 20% aqueous solution of sodium hydroxide. With addition of 0.2 wt. % of alpha-amylase (TERMAMYL 60L, product of NOVO Industry Co., Ltd.), the solution was hydrolyzed at 85° C. for 40 minutes. The hydrolyzate was then autoclaved at 130°0 C. for 10 minutes, thereafter discharged into the atmosphere, cooled to 86° C. and hydrolyzed for 20 minutes with 0.05 wt. % of alpha-amylase added thereto. The resulting hydrolyzate was cooled to a temperature of 55° C., adjusted to a pH of 5.5 and hydrolyzed for 36 hours with 0.2 wt. % of glucoamylase (product of Amano Seiyaku Co., Ltd.) added thereto, whereupon the hydrolyzate was adjusted to a pH of 3.5 to inactivate the glucoamylaze. The hydrolyzate was refined in the same manner as in Example 1 and further treated in the same manner as in Example 1 with the exception of using potassium-type AMBERLITE IR-118 (product of Japan Organo Co., Ltd.) as a strongly acidic ion exchange resin, whereby an indigestible fraction was obtained. This fraction was concentrated to a concentration of 50% and then spray-dried, affording about 4.5 kg of an indigestible dextrin having a moisture content of 4.8%.

Example 3

Commercial potato starch (2500 kg) was placed into a ribbon mixer, and 100 liters of 3% hydrochloric acid solution was sprayed onto the starch with use of pressurized air while rotating the mixer. The mixture was then passed through a disintegrator to obtain a uniform mixture, which was thereafter aged in the ribbon mixer for 10 hours. The mixture was predried to a moisture content of about 3% by a flash drier, subsequently continuously charged into a converter of the rotary kiln type and heat-treated at 180° C. for 25 minutes to obtain a pydrodextin.

Water (5000 liters) was added to the pydrodextrin (2000 kg) to prepare a solution, which was then adjusted to a pH of 5.8 with 20% aqueous solution of sodium hydroxide. With addition of 0.15 wt. % of alpha-amylase (TERMAMYL 60L, product of NOVO Industry Co., Ltd.), the solution was hydrolyzed at 86° C. for 1 hour. The hydrolyzate was then cooled to a temperature of 55° C., adjusted to a pH of 5.6 and hydrolyzed for 36 hours with 0.1 wt. % of glucoamylaze (product of Amano Seiyaku Co., Ltd.) added thereto. The resulting hydrolyzate was adjusted to a pH of 3.5 to inactivate the glucoamylase. The hydrolyzate was thereafter treated in the same manner as in Example 2, giving about 4 kg of an indigestible dextrin having a moisture content of 4.5%.

Example 4

Commercial potato starch (2500 kg) was placed into a ribbon mixer, and 376 liters of 0.5% hydrochloric acid solution was sprayed onto the starch with use of pressurized air while rotating the mixer. The mixture was then passed through a disintegrator to obtain a uniform mixture, which was thereafter aged in the ribbon mixer for 8 hours. The mixture was predried to a moisture content of about 4% by a flash drier, subsequently continuously charged into a converter of the rotary kiln type and heat-treated at 165° C. for 15 minutes to obtain a pyrodextrin. Water (4000 liters) was added to the pyrodextrin (2000 kg) to prepare a solution, which was then adjusted to a pH of 6.0 with 20% aqueous solution of sodium hydroxide. With addition of 0.1 wt. % of alpha-amylase (TERMAMYL 60L, product NOVO Industry Co., Ltd.), the solution was hydrolyzed at 82° C. for 1 hour. The hydrolyzate was then autoclaved at 125° C. for 10 minutes, thereafter discharged into the atmosphere, cooled to a temperature of 57° C., adjusted to a pH 5.5 and hydrolyzed for 36 hours with 0.1 wt. % of glucoamylase (product of Amano Seiyaku Co., Ltd.) added thereto. The resulting hydrolyzate was adjusted to a pH of 3.6 to inactivate the glucoamylase. The hydrolyzate was refined and concentrated in the same manner as in Example 1 to obtain a 52% solution. A 20 liter portion of the solution was passed at 60° C. at SV 0.3 through the column of a continuous chromatographic device packed with 10 liters of DIAION SKK-116 (product of Mitsubishi Chemical Industries, Ltd.), which is a strongly acidic cation exchange resin of the sodium type. Subsequently, water was passed through the column to separate off 71% of glucose formed and obtain an indigestible fraction. The fraction was concentrated to obtain about 8 kg of a liquid indigestible dextrin having a concentration of 70%.

The solutions obtained in Examples 1 to 4 before the separation procedure were checked for glucose content, and the indigestible dextrins obtained in these examples were analyzed to determine the glucose content, amount (%) of glucose removed, contents of various glycosidic linkages (determined by "Hakomori's methylation method") and content of indigestible component. The fraction of each of these dextrins other than glucose was also analyzed to determine the indigestible component, MN as actually measured, MN as calculated from Equation 1, variation of the calculated value from the measured value and MW/MN. The results are collectively listed in Table 20, which also shows the whiteness of each pyrodextrin.

Although, the appearent glucose separation percentages in these four examples are 98.0%, 91.5% 88.3% and 71.1%, respectively.

TABLE 20

| Item | Example 1 | 2 | 3 | 4 |
|---|---|---|---|---|
| Contents of linkage (%) | | | | |
| non-reduced end | 28.4 | 27.2 | 26.1 | 28.2 |
| 1→4 | 33.6 | 34.1 | 32.6 | 34.4 |
| 1→6 | 10.2 | 11.0 | 10.9 | 10.5 |
| 1→3 | 7.8 | 7.2 | 13.1 | 13.5 |
| 1→4, 1→6 | 10.1 | 10.8 | 7.6 | 6.9 |
| 1→3, 1→4 | 1.9 | 1.9 | 2.1 | 2.0 |
| 1→2, 1→4 | 1.7 | 1.8 | 1.7 | 1.6 |
| others | 6.3 | 6.0 | 5.9 | 2.9 |
| Content of glucose before separation (%) | 29.7 | 45.7 | 62.5 | 67.4 |
| Content of glucose after separation (%) | 0.6 | 3.9 | 7.3 | 19.5 |
| Removal amount of glucose (%) | 98.6 | 95.2 | 95.3 | 88.3 |
| Content of indigestible component (%) | 88.6 | 86.7 | 80.9 | 67.6 |
| Component of indigestible portion other than glucose (%) | 89.1 | 90.2 | 87.3 | 84.0 |
| Content of dietary fiber (%) | 35.5 | 27.7 | 21.7 | 16.3 |
| Component of dietary fiber other than glucose (%) | 35.7 | 28.8 | 23.4 | 20.3 |
| Caloric value 1 (kcal/g) | 1.90 | 2.01 | 2.21 | 2.78 |
| Calory other than glucose | 1.88 | 1.85 | 1.92 | 2.00 |
| Caloric value 2 (kcal/g) | 1.35 | 1.45 | 1.67 | 2.26 |
| Calory other than glucose | 1.33 | 1.29 | 1.38 | 1.48 |
| MN measured value | 712 | 784 | 549 | 527 |
| MN culculated value | 778 | 852 | 513 | 438 |
| Difference between calculated value and measurement (%) | +9.3 | +8.7 | −6.5 | −16.9 |
| MW/MN | 62.4 | 54.3 | 46.7 | 42.1 |
| Whiteness (%) | 40.6 | 45.6 | 47.3 | 51.7 |

The variations of the calculated values from the measured values were in the range of +9.3% to −16.9%

The indigestible dextrin of the present invention is usable for almost all foods. The term "foods" as used herein refers collectively to foods for man and feeds for livestock and for use in zoos and for pets. The indigestible dextrin is prepared from starch, is soluble in water, contains dietary fiber, and is usable also as a low calorie bulking agent in foods, so that it is usable in any food wherein dextrin and maltodextrin are usually usable. More specifically, the indigestible dextrin is effectively usable for liquid or powdery beverages such as coffee, black tea, cola and juice; baked products such as bread, cookies, crackers, cakes, pizza and pies; noodles such as wheat noodles, Chinese noodles and buckwheat noodles; pasta such as spaghetti, macaroni and fettuccini; confectionery such as candies, chocolate and chewing gum; doughnut, potato chips and like fried cakes or foods; ices such as ice cream, shakes and sherbets; daily products such as cream, cheese, milk powder, condensed milk, creamy powder, coffee whitener and milk beverages; chilled desserts such as custard pudding, yoghurt, drinkable yoghurt, jelly, mousse and Bavarian; retorted pouched or canned foods such as soups, stew, gratin and curries; seasonings such as bean paste, soy sauce, Worceter sauce, ketchup, mayonnaise, dressing, bouillon and roux; processed meat products such as ham, sausage, hamburger, meatball and corned beef, and these products as frozen; frozen processed foods such as pilafs, croquettes, omelets and doria; processed fishery products such as artificial boiled crab paste and boiled fish paste; processed agricultural products such as dried mashed potatoes, jam, marmalade, peanut butter and peanut; others including food boiled down in soy, rice cakes, rice snacks and fast foods; alcoholic beverages such as wines, cocktails, fizzes and liqueur; etc.

However, the dextrin is difficult to use in emulsified foods of the W/O type, such as margarin, since the dextrin incorporated therein is liable to separate off during preservation.

Further when serving as a low calorie bulking agent, the dextrin can be added to the food of the inventionin in an amount which is not limited insofar as the quality of the food is not impaired. However, if adults in good health take the low calorie bulking agent in an amount of 2 g/kg body weight by way of foods of the invention, diarrhea will occur in half of them, so that the amount of the agent to be taken is preferably not greater than half of this value, i.e., up to about 1 g/kg body weight.

Nevertheless, since the influence on physiological activities differs from person to person, it is most desirable to alter the amount in view of the effect achieved by the ingestion of the low calorie foods.

To check the indigestible dextrin for characterisitics when it is used in foods, chiefly the product of Example 6 was used in the following experiments to obtain characterisitic dats.

Experimental Example 15

A sensory test was conducted to determine the sweetness of the indigestible dextrin in comparison with that of other saccharides and maltodextrin of DE10, with the sweetness of sucrose taken as 100. Table 21 shows the result.

TABLE 21

| Sample | Sweetness |
|---|---|
| Sugar | 100 |
| Glucose | 65 |
| Sorbitol | 50 |
| Maltodextrin (DE10) | 10 |
| Example 1 | 10 |
| Example 3 | 15 |

TABLE 21-continued

| Sample | Sweetness |
| --- | --- |
| Example 4 | 20 |

The indigestible dextrin is about 10 in sweetness, tasting slightly sweet.

Experimental Example 16

A 30% solution of indigestible dextrin was checked for viscosity at temperatures of 10° to 80° C. using a Brookfield type viscosimeter. FIG. 1 shows the result along with the corresponding values of sucrose, gum arabic and maltodextrin.

The symbols in FIG. 1 stand for the following.
: indigestible dextrin of Example 1
: sucrose
: maltodextrin
○: gum arabic The indigestible dextrin is comparable to maltodextrin in viscosity. This indicates that the indigestible dextrin is usable in foods without entailing a great increase in viscosity.

Experimental Example 17

Coloration due to heating in the presence of amino acid

Figure 2:
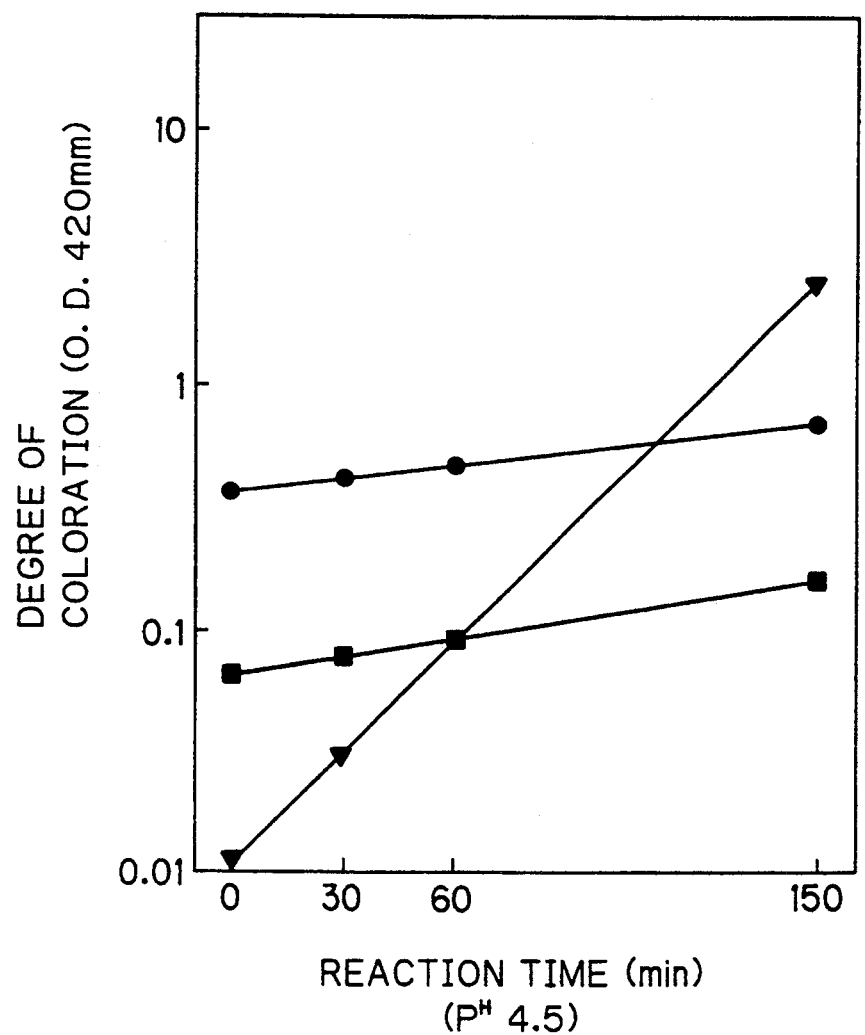
Figure 3:
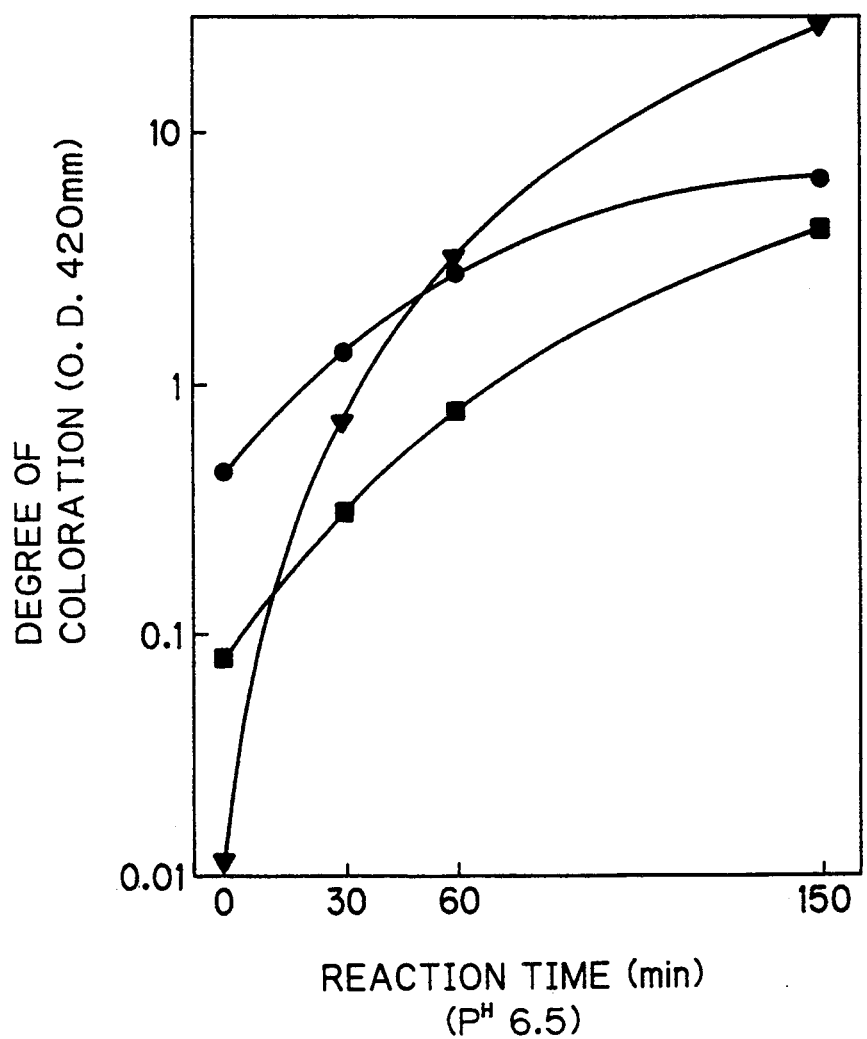

To 10% aqueous solution of indigestible dextrin was added 1% (based on solids) on glycine, and the mixture was heated at 100° C. for 150 minutes and checked for changes in the degree of coloration. The results achieved at pH of 4.5 and pH of 6.5 are shown in FIGS. 2 and 3, respectively. The same smbols as in FIG. 1 were used in these drawings.

The indigestible dextrin is not greatly different in the increase of coloration degree from glucose or maltose. This indicates that the indigestible dextrin is usable generally in the same manner as these materials.

Experimental Example 18

Freezing and thawing

Figure 4:
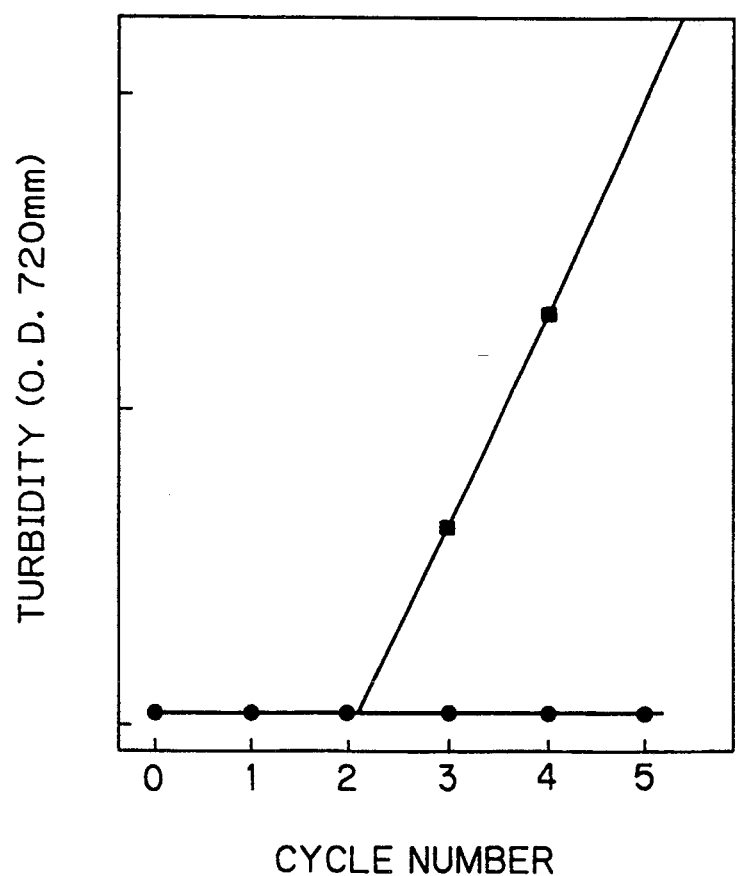

A 30% aqueous solution of indigestible dextrin was subjected to five repeated freeze-thaw cycles and then checked for resulting turbidity. FIG. 4 shows the result along with the result achieved by maltodextrin. The symbols used in FIG. 4 have the same meaning as in FIG. 1.

The indigestible dextrin is much less than maltodextrin in increases in turbidity and is therefore very suitable for use in frozen foods.

Experimental Example 19

Freezing point depression

Figure 5:
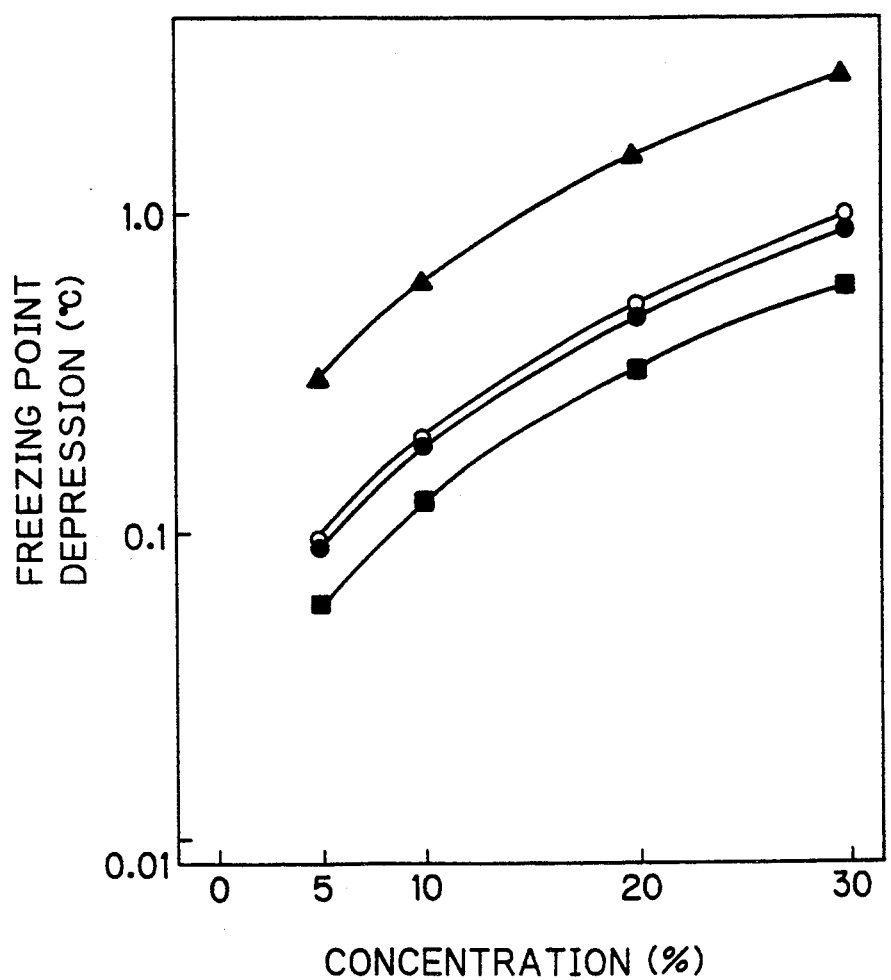

FIG. 5 shows the result obtained by checking 5 to 30% aqueous solutions of indigestible dextrin for freezing point depression along with the result achieved by sucrose and maltodextrin. The symbols in FIG. 5 are the same as in FIG. 1.

The indigestible dextrin is generally intermediate between sugar and maltodextrin in the degree of freezing point depression and is therefore suited to use in ices and the like.

Experimental Example 20

Hygroscopicity

Figure 6:
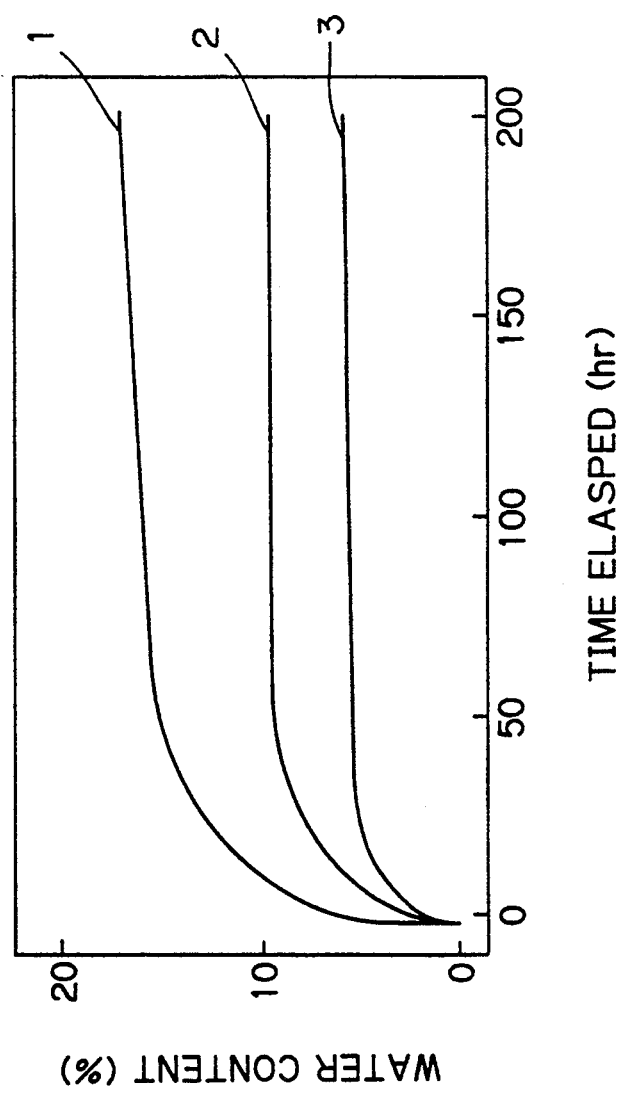

The indigestible dextrin was made anhydrous by drying and then allowed to stand in a constant-humidity container at 20° C. and a relative humidity of 81%, 52% or 32% for 200 hours. FIG. 6 shows the hygroscopicity of the indigestible dextrin thus determined.

In FIG. 6, the results obtained at R.H. 81%, R.H. 52% and R.H. 32% are indicated at (1), (2) and (3), respectively.

The water content of the indigestible dextrin will not exceed 18% even if preserved For a long period of time. The indigestible dextrin is therefore suited to use in powdery foods.

Experimental Example 21

Mixography

Figure 7:
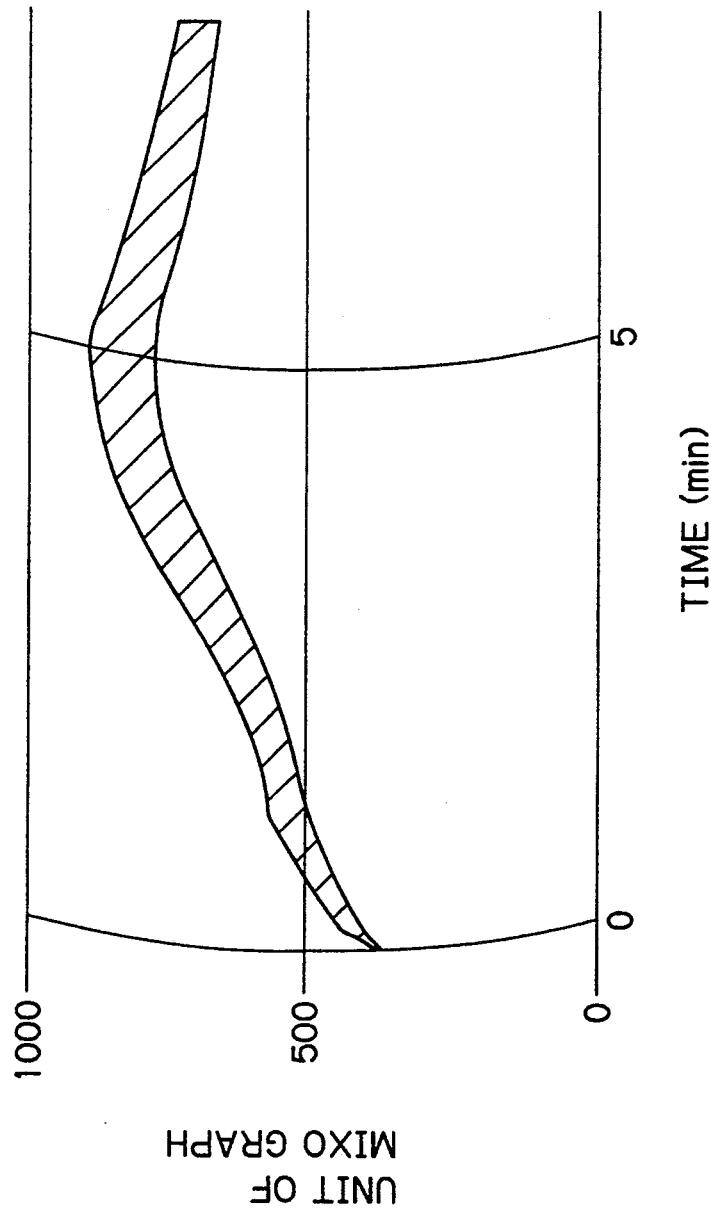
Figure 8:
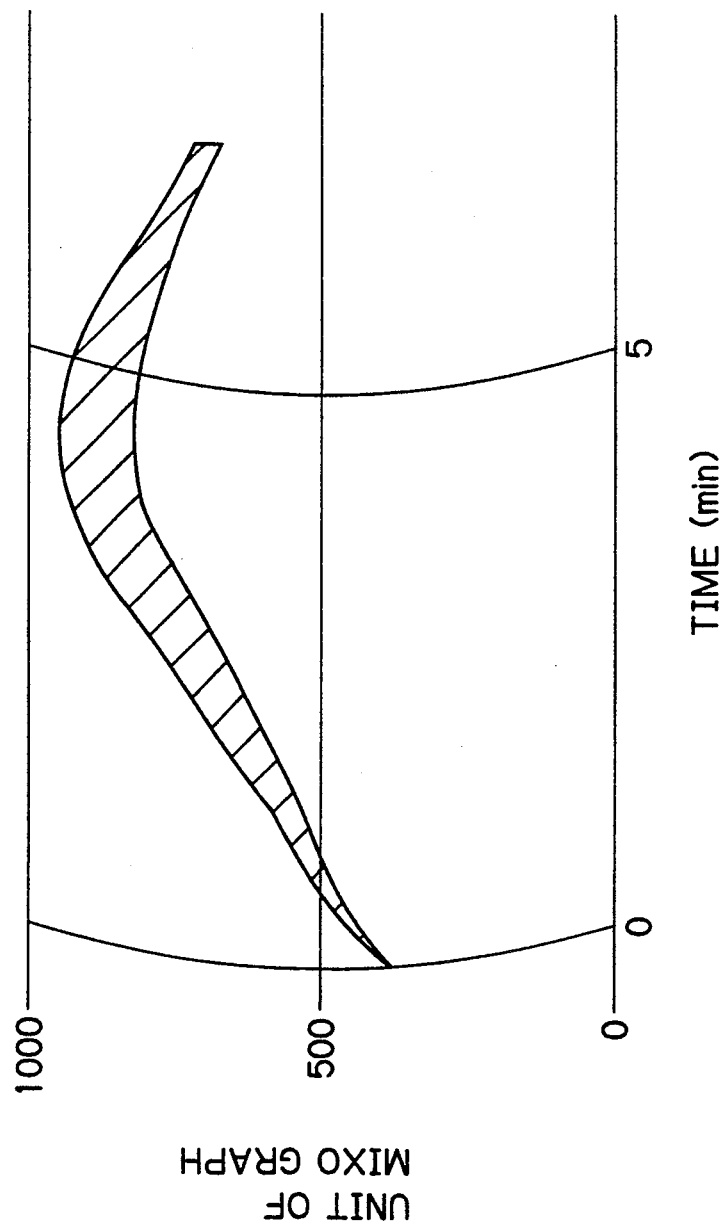

To investigate the behavior of the indigestible dextrin for use in foods having wheat flour incorporated therein, mixograms were prepared using the mixes given in Table 22. FIGS. 7 to 9 show the results. FIG. 7 shows a control mix; FIG. 8, a sugar mix and FIG. 9, an indigestible dextrin of example 1 mix (low calorie mix containing dietary fiber).

TABLE 22

|  | Control | Sugar | Example 1 |
| --- | --- | --- | --- |
| Hard flour (g) | 35.0 | 35.0 | 35.0 |
| Sugar (g) | — | 1.75 | — |
| Example 6 (g) | — | — | 1.75 |
| Water (g) | 26.0 | 25.5 | 25.5 |
| Ratio of water added (%) | 74.3 | 72.9 | 72.9 |
| Developing time (min) | 4.5 | 4.0 | 5.5 |

In the case where the indigestible dextrin was used in place of sucrose, the mix became viscoelastic with a 1.5 minute delay. It was therefore found necessary to lengthen the dough mixing time, to age the dough for a longer period of time or to add the indigestible dextrin during mixing.

Examples of foods embodying the invention will be described next. The indigestible dextrin used will be referred to by the number of example in which it was prepared. The amounts of ingredients and dietary fiber are expressed in grams.

Example 5

Food example 1

Black tea of the composition given in Table 23 was prepared.

TABLE 23

| Black tea | Control | Example |
| --- | --- | --- |
| Black tea extract | 97.0 | 97.0 |
| Sugar | 3.0 | 3.0 |
| Dextrin (Example 3) | — | 8.0 |
| Dietary fiber | 0 | 1.66 |
| Dietary fiber/240 g | 0 | 3.69 |

Example 6

Food example 2

Cola drink of the composition given in Table 24 was prepared.

TABLE 24

| Cola drink | Control | Example |
| --- | --- | --- |
| Sugar | 10.0 | 10.0 |
| Cola base | 0.3 | 0.3 |
| Citric acid | 0.05 | 0.05 |
| Soda water | 89.65 | 89.65 |
| Dextrin (Example 1) | — | 10.0 |
| Dietary fiber | 0 | 3.40 |

TABLE 24-continued

| Cola drink | Control | Example |
|---|---|---|
| Dietary fiber/240 g | 0 | 7.42 |

Example 7

Food example 3

Orange juice (30%) was prepared according to the recipe given in Table 25 dissolving powdery ingredients in water, adding concentrated juice and flavoring to the solution and homogenizing the mixture by a homomixer.

TABLE 25

| Orange juice (30%) | Control | Example |
|---|---|---|
| Orange juice concentrate (BX.45) | 6.7 | 6.7 |
| Sugar | 8.1 | 8.1 |
| Citric acid | 0.3 | 0.3 |
| Sodium citrate | 0.1 | 0.1 |
| Orange flavor | 0.3 | 0.3 |
| Water | 84.5 | 84.5 |
| Dextrin (Example 1) | — | 4.0 |
| Dietary fiber | 0.07 | 1.43 |
| Dietary fiber/240 g | 0.17 | 3.30 |

Example 8

Food example 4

A sports drink was prepared by mixing all ingredients with water according to the recipe of Table 26 and sterilizing the mixture by heating.

TABLE 26

| Sports drink | Control | Example |
|---|---|---|
| Salt | 0.5 | 0.5 |
| Vitamin C | 0.03 | 0.03 |
| Vitamin B$_1$.Sodium salt | 0.03 | 0.03 |
| Magnesium chloride | 0.2 | 0.2 |
| Calcium lactate | 0.2 | 0.2 |
| Citric acid | 2.4 | 2.4 |
| Sodium citrate | 1.7 | 1.7 |
| Flavor | 2.0 | 2.0 |
| Dextrose | 80.0 | 80.0 |
| Fructose | 12.94 | 12.94 |
| Water | 1500.0 | 1500.0 |
| Dextrin (Example 1) | — | 55.0 |
| Total | 1600.0 | 1655.0 |
| Dietary fiber | 0 | 18.7 |
| Dietary fiber/240 g | 0 | 2.71 |

Example 9

Food example 5

According to the recipe of Table 27, a milk shake was prepared by mixing all ingredients with water, heating the mixture to 80° C. for dissolving, homogenizing the butter by a homogenizer, aging the mixture overnight at 5° C., then freezing the mixture, thereafter rapidly cooling the mixture to −40° C. fully shaking the mixture.

TABLE 27

| Milk shake | Control | Example |
|---|---|---|
| Butter | 7.0 | 2.0 |
| Skimmed milk | 9.1 | 5.2 |
| Dextrin (Example 3) | — | 17.65 |
| Sugar | 9.0 | — |
| Aspartame | — | 0.05 |
| Milk flavor | — | 0.1 |
| Butter flavor | — | 0.1 |
| Sorbitol | 4.0 | 4.0 |
| Emulsifier | 0.7 | 0.7 |

TABLE 27-continued

| Milk shake | Control | Example |
|---|---|---|
| Water | 70.2 | 70.2 |
| Dietary fiber | 0.08 | 3.70 |
| Dietary fiber/250 g | 0.20 | 9.25 |
| Caloric val. 1 (KCal/100 g) | 134 | 88 |
| Caloric val. 2 (KCal/100 g) | 134 | 78 |

Example 10

Food example 6

According to the recipe of Table 28, ice cream was prepared by mixing all ingredients together, heating the mixture to 70° C., stirring the mixture by a homomixer, thereafter homogenizing the mixture by a homogenizer, aging the mixture in a refrigerator for 1 day, freezing the mixture and thereafter rapidly cooling the mixture to −40° C.

TABLE 28

| Ice cream | Control | Example |
|---|---|---|
| Butter | 15.0 | 5.0 |
| Skimmed milk | 8.0 | 5.0 |
| Sugar | 12.0 | — |
| Dextrin (Example 1) | — | 26.77 |
| Emulsifier | 0.5 | 0.5 |
| Milk flavor | — | 0.1 |
| Cream flavor | — | 0.1 |
| Water | 57.5 | 57.5 |
| Aspartame | — | 0.03 |
| Sorbitol | — | 5.0 |
| Maltodextrin (DE 8) | 7.0 | — |
| Dietary fiber | 0.07 | 9.15 |
| Dietary fiber/150 g | 0.11 | 13.73 |
| Caloric val. 1 (KCal/100 g) | 216 | 123 |
| Caloric val. 2 (KCal/100 g) | 216 | 108 |

Example 11

Food example 7

According to the recipe of Table 29, fermented skimmed milk, was mixed with other ingredients, and the mixture was treated by a homogenizer to prepare a yoghurt drink.

TABLE 29

| Yoghurt (Soft) | Control | Example |
|---|---|---|
| Fermented skimmed milk | 38.0 | 38.0 |
| Sugar | 13.0 | 13.0 |
| Stabilizer | 0.35 | 0.35 |
| Flavor | 0.05 | 0.05 |
| Water | 48.6 | 38.6 |
| Dextrin (Example 4) | — | 10.0 |
| Dietary fiber | 0.03 | 1.17 |
| Dietary fiber/240 g | 0.07 | 2.81 |

Example 12

Food example 8

According to the recipe of Table 30, hard yoghurt was prepared by adding a hardening agent to skimmed milk, innoculating the mixture with 3% of starter, refrigerating the mixture when acidity of 0.7% was attained, mixing the mixture with other ingredients by stirring and refrigerating the resulting mixture again.

TABLE 30

| Yoghurt (Hard) | Control | Example |
|---|---|---|
| Skimmed milk | 87.0 | 87.0 |
| Sugar | 13.0 | — |
| Dextrin (Example 1) | — | 13.0 |
| Stevioside | — | 0.05 |

TABLE 30-continued

| Yoghurt (Hard) | Control | Example |
|---|---|---|
| Flavor | Small amt. | Small amt. |
| Gelatin | Small amt. | Small amt. |
| Dietary fiber | 0.07 | 4.49 |
| Dietary fiber/150 g | 0.11 | 6.74 |
| Caloric val. 1 (KCal/100 g) | 78 | 52 |
| Caloric val. 2 (KCal/100 g) | 78 | 45 |

Example 13

Food example 9

According to the recipe of Table 31, a powder of coffee whitener was prepared by dissolving water-soluble ingredients in 66.6% of hot water based on the dry weight of the ingredients, dissolving an emulsifying agent in oil, mixing together and homogenizing the two solutions at 60° C. To obtain an emulsion, and thereafter spray-drying the emulsion.

TABLE 31

| Coffee whitener | Control | Example |
|---|---|---|
| Hardened soy bean oil | 47.0 | 47.0 |
| Corn syrup solid (DE 40) | 52.0 | — |
| Emulsifier | 0.84 | 0.84 |
| Cream flavor | 0.16 | 0.16 |
| Dextrin (Example 2) | — | 52.0 |
| Dietary fiber | 0 | 13.7 |
| Dietary fiber/12 g | 0 | 1.65 |
| Caloric val. 1 (KCal/100 g) | 640 | 541 |
| Caloric val. 2 (KCal/100 g) | 640 | 514 |

Example 14

Food example 10

Candy was prepared by dissolving the ingredients of Table 32 other than the flavor in water, concentrating the solution to Bx 80°, boiling down the concentrate by an evaporator, cooling the resulting concentrate to 40° C., admixing the flavor therewith and molding the mixture.

TABLE 32

| Candy | Control | Example |
|---|---|---|
| Corn syrup | 44.4 | 22.2 |
| Citric acid | 0.5 | 0.5 |
| Flavor | 0.1 | 0.1 |
| Sugar | 55.0 | 22.5 |
| Dextrin (Example 3) | — | 54.6 |
| Stevioside | — | 0.1 |
| Dietary fiber | 0 | 11.3 |
| Dietary fiber/12 g | 0 | 1.36 |
| Caloric val. 1 (KCal/100 g) | 362 | 280 |
| Caloric val. 2 (KCal/100 g) | 362 | 252 |

Example 15

Food example 11

The ingredients of Table 33 other than the carbohydrates and flavor were placed into a pan, heated for melting and thoroughly mixed together. Chewing gum was prepared by admixing the carbohydrates with the mixture as cooled to 50° C., followed by addition of the flavor at 40° C., molding and standing for cooling.

TABLE 33

| Chewing gum | Control | Example |
|---|---|---|
| Poly-Vinylacetate | 22.0 | 22.0 |
| Plasticizer | 2.5 | 2.5 |
| Poly-isobutyrene | 2.5 | 2.5 |
| Micro-crystalline wax | 2.0 | 2.0 |

TABLE 33-continued

| Chewing gum | Control | Example |
|---|---|---|
| Calcium carbonate | 3.0 | 3.0 |
| Sugar (powder) | 47.0 | — |
| Dextrose | 20.0 | — |
| Dextrin (Example 2) | — | 66.7 |
| Aspartame | — | 0.3 |
| Flavor | 1.0 | 1.0 |
| Dietary fiber | 0 | 17.6 |
| Dietary fiber/32 g | 0 | 5.63 |
| Caloric val. 1 (KCal/100 g) | 263 | 138 |
| Caloric val. 2 (KCal/100 g) | 263 | 102 |

Example 16

Food example 12

All ingredients of Table 34 were thoroughly mixed together at 40° C. and further kneaded in an attritor for a long period of time to pulverize the particles, followed by molding and cooling to prepare a sweet chocolate.

TABLE 34

| Sweet chocolate | Control | Example |
|---|---|---|
| Bitter chocolate | 30.0 | 30.0 |
| Sugar | 55.0 | — |
| Dextrin (Example 1) | — | 54.7 |
| Aspartame | — | 0.3 |
| cacao butter | 15.0 | 15.0 |
| Dietary fiber | 0.0 | 18.6 |
| Dietary fiber/100 g | 0.0 | 18.6 |
| Caloric val. 1 (KCal/100 g) | 479 | 369 |
| Caloric val. 2 (KCal/100 g) | 479 | 344 |

Example 17

Food example 13

According to the recipe of Table 35, wheat flour, modified starch and egg yolk powder were admixed with a small amount of water. A solution of the other materials as dissolved in the remaining portion of water at 80° C. was added to the mixture while using a whip, and the resulting mixture was boiled on an intense fire to prepare custard cream.

TABLE 35

| Custard cream | Control | Example |
|---|---|---|
| Sugar | 14.0 | — |
| Dextrose | 10.0 | — |
| Corn syrup (DE 40) | 12.0 | 6.0 |
| Water | 38.8 | 38.8 |
| Dextrin (Example 3) | — | 33.9 |
| Stevioside | — | 0.1 |
| Wheat flour | 4.0 | 4.0 |
| Modified starch | 7.0 | 7.0 |
| Skimmed milk | 2.0 | 2.0 |
| Margarine | 12.0 | 8.0 |
| Egg yolk powder | 0.2 | 0.2 |
| Dietary fiber | 0.12 | 7.14 |
| Dietary fiber/50 g | 0.06 | 3.57 |
| Caloric val. 1 (KCal/100 g) | 266 | 200 |
| Caloric val. 2 (KCal/100 g) | 266 | 183 |

Example 18

Food example 14

According to the recipe of Table 36, gelatine was dissolved in 25 g of water, and all the other ingredients except aspartame were dissolved in the remaining portion of water. The solutions were cooled to 40° C., then all the ingredients were mixed together, and the resulting mixture was refrigerated to prepare an orange jelly.

TABLE 36

| Orange gelly | Control | Example |
| --- | --- | --- |
| Sugar | 18.0 | — |
| Dextrin (Example 2) | — | 18.0 |
| Aspartame | — | 0.11 |
| Water | 37.5 | 37.5 |
| Gelatine | 2.8 | 2.8 |
| Orange juice | 31.2 | 31.2 |
| Curacao | 10.4 | 10.4 |
| Dietary fiber | 0.09 | 4.84 |
| Dietary fiber/100 g | 0.09 | 4.84 |
| Caloric val. 1 (KCal/100 g) | 120 | 85 |
| Caloric val. 2 (KCal/100 g) | 120 | 76 |

Example 19

Food example 15

According to the recipe of Table 37, the ingredients other than pectin were mixed together, lightly crushed by a mixer and then heated on a low fire. Upon evaporation of 20% of the water, pectin was added to the mixture, followed by cooling to prepare strawberry jam.

TABLE 37

| Strawberry jam | Control | Example |
| --- | --- | --- |
| Flesh strawberry | 60.0 | 60.0 |
| Sugar | 40.0 | — |
| Dextrin (Example 1) | — | 40.0 |
| Pectin | 0.1 | 0.1 |
| Citric acid | 0.1 | 0.1 |
| Aspartame | — | 0.25 |
| Dietary fiber | 1.00 | 14.6 |
| Dietary fiber/30 g | 0.46 | 6.67 |
| Caloric val. 1 (KCal/100 g) | 267 | 147 |
| Caloric val. 2 (KCal/100 g) | 267 | 113 |

Example 20

Food example 16

According to the recipe of Table 38, granulated sugar, water and indigestible dextrin were added to pared apples, and the mixture was boiled on a medium fire. When the apples became semi-transparent, lemon juice was added to the mixture, followed by boiling down on a medium fire without scorching. When the apples became soft, the mixture was strained and further boiled down to Bx 70° C. To prepare apple jam.

TABLE 38

| Apple jam | Control | Example |
| --- | --- | --- |
| Flesh apple | 60.0 | 60.0 |
| Sugar | 19.4 | 19.4 |
| Lemon juice | 2.2 | 2.2 |
| Water | 18.4 | 18.4 |
| Dextrin (Example 3) | — | 10.0 |
| Dietary fiber | 0.96 | 3.03 |
| Dietary fiber/30 g | 0.72 | 1.68 |

Example 21

Food example 17

According to the recipe of Table 39, the whole amount of indigestible dextrin and stevioside were added to 30 g of water to prepare a syrup, which was then heated. When the syrup became boiled up, bean paste was added thereto. The mixture was boiled down to an amount weighing 100 g to prepare bean jam.

TABLE 39

| Bean jam | Control | Example |
| --- | --- | --- |
| Bean paste | 63.0 | 63.0 |

TABLE 39-continued

| Bean jam | Control | Example |
| --- | --- | --- |
| Sugar | 37.0 | — |
| Dextrin (Example 3) | — | 36.77 |
| Stevioside | — | 0.23 |
| Dietary fiber | 4.54 | 12.2 |
| Dietary fiber/100 g | 4.54 | 12.2 |
| Caloric val. 1 (KCal/100 g) | 240 | 176 |
| Caloric val. 2 (KCal/100 g) | 240 | 157 |

Example 22

Food example 18

According to the recipe given in Table 40, 23.6 g of water, indigestible dextrin and stevioside were added to agar-agar swollen with water, and the mixture was heated for boiling and dissolving, strained and then boiled again, followed by addition of bean paste. The mixture was boiled down to an amount weighing 100 g, then moled and cooled to prepare a sweet jelly of beans.

TABLE 40

| Sweet jelly of beans | Control | Example |
| --- | --- | --- |
| Bean paste | 42.0 | 42.0 |
| Agar-agar | 0.8 | 0.8 |
| Water | 7.2 | 7.2 |
| Sugar | 50.0 | — |
| Dextrin (Example 3) | — | 49.7 |
| Stevioside | — | 0.3 |
| Dietary fiber | 3.02 | 16.1 |
| Dietary fiber/40 g | 1.21 | 6.46 |
| Caloric val. 1 (KCal/100 g) | 257 | 161 |
| Caloric val. 2 (KCal/100 g) | 257 | 135 |

Example 23

Food example 19

A cereal was dipped in a solution of indigestible dextrin, Bx 50°, according to the recipe of Table 41 and dried overnight at 40° C. to prepare a processed cereal. The product was glossier than a control, and the original water retentivity of 2.7% increased to 7.0%.

TABLE 41

| Cereal | Control | Example |
| --- | --- | --- |
| Cereal | 100.0 | 60.0 |
| Dextrin (Example 3) | — | 40.0 |
| Dietary fiber | 2.90 | 10.0 |
| Dietary fiber/40 g | 1.16 | 4.01 |
| Caloric val. 1 (KCal/100 g) | 389 | 317 |
| Caloric val. 2 (KCal/100 g) | 389 | 297 |

Example 24

Food example 20

According to the recipe given in Table 42, indigestible dextrin was uniformly kneaded with wheat flour and further kneaded therewith while adding water in small portions to prepare spaghetti.

TABLE 42

| Spaghetti | Control | Example |
| --- | --- | --- |
| Wheat flour | 100.0 | 90.0 |
| Water | 30.0 | 25.0 |
| Dextrin (Example 4) | — | 15.0 |
| Dietary fiber | 2.10 | 3.60 |
| Dietary fiber/200 g | 3.23 | 5.54 |

Example 25

Food example 21

The ingredients of Table 43 were fully kneaded together to obtain dough, which was then fermented and baked to prepare loaves of bread.

TABLE 43

| White bread | Control | Example |
| --- | --- | --- |
| Wheat flour | 100.0 | 95.0 |
| Water | 60.0 | 56.0 |
| Baker's yeast | 3.0 | 3.0 |
| Salt | 2.0 | 1.5 |
| Sugar | 5.0 | 4.5 |
| Skimmed milk | 4.0 | 3.0 |
| Shortening | 6.0 | 5.0 |
| Dextrin (Example 4) | — | 12.0 |
| Dietary fiber/180 g | 2.14 | 3.39 |

Example 26

Food example 22

According to the recipe of Table 44, milk and eggs were added to wheat flour, and the other ingredients were added to the mixture with kneading to obtain uniform dough, which was then molded and fried in oil at 160° to 180° C. while turning the molded pieces upside down. The fried pieces were drained off the oil to obtain American doughnut.

TABLE 44

| American doughnut | Control | Example |
| --- | --- | --- |
| Wheat flour | 100.0 | 90.0 |
| Sugar | 25.0 | 22.5 |
| Egg (Whole) | 25.0 | 22.5 |
| Milk | 42.0 | 37.0 |
| Butter | 4.6 | 4.6 |
| Salt | 0.2 | 0.2 |
| Lemon flavor | 0.2 | 0.2 |
| Baking powder | 3.0 | 3.0 |
| Dextrin (Example 4) | — | 20.0 |
| Dietary fiber | 2.21 | 4.27 |
| Dietary fiber/100 g | 1.11 | 2.14 |

Example 27

Food example 23

According to the recipe of Table 45, egg white and water were fully mixed together to obtain a whipped mixture, to which indigestible dextrin, Avicel and hard wheat flour were successively added with kneading to prepare a uniform mixture, The mixture was freeze-dried to avoid thermal denaturation of the egg white and prepare a replacer for wheat flour.

TABLE 45

| Wheat flour replacer | Control | Example |
| --- | --- | --- |
| Soft wheat flour | 100.0 | — |
| Dextrin (Example 1) | — | 35.0 |
| Egg white | — | 10.0 |
| Water | — | 20.0 |
| Avicel | — | 20.0 |
| Hard wheat flour | — | 15.0 |
| Dietary fiber | 2.10 | 32.3 |
| Caloric val. 1 (KCal/100 g) | 368 | 157 |
| Caloric val. 2 (KCal/100 g) | 368 | 138 |

Example 28

Food example 24

All ingredients listed in Table 46 and including the flour replacer of food example 23 were kneaded together. The mixture, when becoming elastic, was spread out flat and blanked out. The resulting pieces were baked at 190° C. for 10 minutes, affording butter cookies.

TABLE 46

| Butter cookie | Control | Example |
| --- | --- | --- |
| Wheat flour | 45.0 | — |
| Wheat flour replacer | — | 45.0 |
| Sugar | 21.0 | — |
| Dextrin (Example 1) | — | 27.0 |
| Stevioside | — | 0.1 |
| Shortening | 22.0 | 15.9 |
| Water | 12.0 | 12.0 |
| Dietary fiber | 0.95 | 23.7 |
| Dietary fiber/30 g | 0.29 | 7.12 |
| Caloric val. 1 (KCal/100 g) | 449 | 267 |
| Caloric val. 2 (KCal/100 g) | 449 | 244 |

Example 29

Food example 25

According to the recipe of Table 47, all ingredients including the flour replacer of food example 23 were mixed with water and treated with a whip for stirring and dissolving to obtain uniform dough, which was then baked at 180° for 50 minutes to prepare a pound cake.

TABLE 47

| Pound cake | Control | Example |
| --- | --- | --- |
| Wheat flour | 25.0 | — |
| Wheat flour replacer | — | 25.0 |
| Sugar | 25.0 | — |
| Dextrin (Example 3) | — | 33.4 |
| Stevioside | — | 0.1 |
| Egg (whole) | 18.0 | 18.0 |
| Milk | 8.0 | 8.0 |
| Shortening | 17.0 | 8.5 |
| Water | 7.0 | 7.0 |
| Dietary fiber | 0.56 | 15.0 |
| Dietary fiber/100 g | 0.56 | 15.0 |
| Caloric val. 1 (KCal/100 g) | 379 | 222 |
| Caloric val. 2 (KCal/100 g) | 379 | 200 |

Example 30

Food example 26

According to the recipe of Table 48, all ingredients including the flour replacer of food example 23 were mixed with water, and the mixture was stirred with a whip to incorporate foams into the mixture. The mixture was baked at 180° C. for 40 minutes to prepare a sponge cake.

TABLE 48

| Sponge cake | Control | Example |
| --- | --- | --- |
| Wheat flour | 30.0 | — |
| Wheat flour replacer | — | 30.0 |
| Sugar | 35.0 | — |
| Egg (whole) | 35.0 | 35.0 |
| Dextrin (Example 3) | — | 34.9 |
| Stevioside | — | 0.1 |
| Dietary fiber | 0.67 | 17.0 |
| Dietary fiber/100 g | 0.67 | 17.0 |
| Caloric val. 1 (KCal/100 g) | 302 | 178 |
| Caloric val. 2 (KCal/100 g) | 302 | 154 |

Example 31

Food example 27

According to the recipe of Table 49, crust dough was prepared by full kneading and repeated folding. The inner ingredient was boiled down until it became half-deformed. The dough and inner ingredient were molded and then baked to prepare an apple pie.

TABLE 49

| Apple pie | Control | Example |
|---|---|---|
| Soft wheat flour | 80.0 | 70.0 |
| Hard wheat flour | 120.0 | 110.0 |
| Butter | 180.0 | 170.0 |
| Water | 109.0 | 92.0 |
| Apple | 300.0 | 290.0 |
| Sugar | 100.0 | 100.0 |
| Cinnamon powder | 1.0 | 1.0 |
| Egg yolk | 10.0 | 10.0 |
| Dextrin (Example 4) | — | 57.0 |
| Dietary fiber | 9.01 | 14.9 |
| Dietary fiber (1/6) | 1.50 | 2.49 |

Example 32

Food example 28

According to the recipe of Table 50, corn cream soup was prepared by boiling corn in water until no unboiled portion remained, then adding the other ingredients and boiling down the mixture.

TABLE 50

| Corn cream Soup | Control | Example |
|---|---|---|
| Milk | 19.8 | 19.8 |
| Sweet corn | 18.4 | 18.4 |
| Butter | 2.3 | 2.3 |
| Wheat flour | 2.0 | 2.0 |
| Salt | 1.0 | 1.0 |
| Seasonings | 0.2 | 0.2 |
| Spices | 0.2 | 0.2 |
| Water | 56.1 | 48.1 |
| Dextrin (Example 4) | — | 8.0 |
| Dietary fiber | 0.45 | 1.36 |
| Dietary fiber/200 g | 0.90 | 2.72 |

Example 33

Food example 29

According to the recipe given in Table 51, spare rib was pan-fried and placed into another pan. Vegetables were also pan-fried and transferred onto the pan. Wheat flour and curry powder were pan-fried into a brown roux. All the ingredients were boiled down in the pan to prepare a retorted curry.

TABLE 51

| Retorted pauch curry | Control | Example |
|---|---|---|
| Spare rib | 14.0 | 13.0 |
| Salt | 0.5 | 0.5 |
| Butter | 5.0 | 5.0 |
| Water | 46.0 | 45.0 |
| Potato | 14.0 | 13.0 |
| Onion | 12.0 | 11.0 |
| Carrot | 3.0 | 2.0 |
| Wheat flour | 4.0 | 4.0 |
| Curry powder | 0.5 | 0.5 |
| Spices | 0.5 | 0.5 |
| Dextrin (Example 1) | — | 5.0 |
| Dietary fiber | 0.62 | 2.26 |
| Dietary fiber/200 g | 1.24 | 4.52 |

Example 34

Food example 30

According to the recipe of Table 52, meat was fully pan-fried and then placed into another pan. Vegetables, especially onions, were fully pan-fried. All the ingredients were then boiled down in the pan for 3 hours to prepare beef stew.

TABLE 52

| Beef stew | Control | Example |
|---|---|---|
| Spare rib | 15.5 | 15.5 |
| Salt | 0.2 | 0.2 |
| Wheat flour | 2.7 | 2.7 |
| Salad oil | 3.9 | 3.9 |
| Onion | 9.7 | 9.7 |
| Potato | 13.6 | 13.6 |
| Carrot | 5.8 | 5.8 |
| Green beans | 1.9 | 1.9 |
| Seasoning (liquid) | 38.8 | 33.8 |
| Butter | 1.9 | 1.9 |
| Tomato puree | 5.8 | 5.8 |
| White pepper | 0.2 | 0.2 |
| Dextrin (Example 4) | — | 5.0 |
| Dietary fiber | 0.78 | 1.35 |
| Dietary fiber/300 g | 2.34 | 4.05 |

Example 35

Food example 31

Non-oil dressing was prepared according to the recipe of Table 53 by mixing liquid ingredients together and thereafter dissolving powder ingredients in the mixture.

TABLE 53

| Non-oil dressing | Control | Example |
|---|---|---|
| Vinegar | 33.0 | 33.0 |
| Sugar | 2.0 | 2.0 |
| Salt | 0.5 | 0.5 |
| Soy-sauce | 8.4 | 8.4 |
| Seasoning (liquid) | 26.3 | 26.3 |
| Corn sirup solid | 29.8 | — |
| Dextrin (Example 1) | — | 29.8 |
| Dietary fiber | 0 | 10.1 |
| Dietary fiber/20 g | 0 | 2.03 |
| Caloric val. 1 (KCal/100 g) | 155 | 96 |
| Caloric val. 2 (KCal/100 g) | 155 | 80 |

Example 36

Food example 32

According to the recipe of Table 54, powder ingredients other than Xanthan gum were dissolved in water, and the solution was heated to 80° C. Upon the solution reaching 40° C., vinegar was added, and the mixture was treated by a homomixer driven at a medium speed while adding salad oil in small portions to the mixture to obtain an emulsion. Xanthan gum was dissolved in the emulsion with the homomixer driver at a low speed to prepare dressing of the emulsion type.

TABLE 54

| Dressing | Control | Example |
|---|---|---|
| Salad oil | 28.0 | 14.0 |
| Emulstar #30 | 3.0 | 3.0 |
| Xanthan gum | 0.2 | 0.2 |
| Vinegar | 17.0 | 17.0 |
| Salt | 1.3 | 1.3 |
| Sugar | 2.7 | 2.7 |
| Dextrin (Example 1) | — | 14.0 |
| Water | 47.8 | 47.8 |
| Dietary fiber | 0.20 | 4.96 |
| Dietary fiber/20 g | 0.04 | 0.99 |
| Caloric val. 1 (KCal/100 g) | 282 | 179 |
| Caloric val. 2 (KCal/100 g) | 282 | 172 |

"Emulster #30" listed in Table 54 is a trade name for a lipophilic modified starch (product of Matsutani Chemical Industry Co., Ltd.).

Example 37

Food example 33

According to the recipe of Table 55, powder ingredients were dissolved in water and vinegar, and egg yolk was admixed with the solution. The mixture was treated by a homomixer driven at a medium speed while adding salad oil thereto in small portions for emulsification to prepare mayonnaise.

TABLE 55

| Mayonnaise | Control | Example |
|---|---|---|
| Salad oil | 68.0 | 34.0 |
| Vinegar | 12.0 | 11.0 |
| Egg yolk | 17.5 | 10.0 |
| Salt | 1.5 | 1.5 |
| Sugar | 1.0 | 1.0 |
| Dextrin (Example 1) | — | 23.0 |
| Water | — | 19.5 |
| Dietary fiber | 0.02 | 7.83 |
| Dietary fiber/20 g | 0.004 | 1.57 |
| Caloric val. 1 (KCal/100 g) | 696 | 397 |
| Caloric val. 2 (KCal/100 g) | 696 | 385 |

Example 38

Food example 34

Peanut butter was prepared according to the recipe of Table 56 by crushing raw peanut, crushing the peanut with an attritor and admixing other ingredients therewith.

TABLE 56

| Peanut butter | Control | Example |
|---|---|---|
| Peanut | 60.0 | 40.0 |
| Palm oil | 40.0 | 26.0 |
| Dextrin (Example 1) | — | 33.9 |
| Peanut flavor | — | 0.1 |
| Dietary fiber | 5.22 | 15.0 |
| Dietary fiber/20 g | 1.04 | 3.00 |
| Caloric val. 1 (KCal/100 g) | 705 | 526 |
| Caloric val. 2 (KCal/100 g) | 705 | 508 |

Example 39

Food example 35

The powder ingredients listed in the recipe of Table 57 were uniformly mixed together to prepare cheese powder.

TABLE 57

| Cheese powder | Control | Example |
|---|---|---|
| Cheese powder | 100.0 | 40.0 |
| Dextrin (Example 2) | — | 59.9 |
| Cheese flavor | — | 0.1 |
| Dietary fiber | 0.60 | 16.1 |
| Dietary fiber/10 g | 0.06 | 1.61 |
| Caloric val. 1 (KCal/100 g) | 562 | 340 |
| Caloric val. 2 (KCal/100 g) | 562 | 308 |

Example 40

Food example 36

According to the recipe of Table 58, lactobacillus starter and rennet were added to a mixture of fresh cream and indigestible dextrin, followed by standing at 20° C. for 15 hours. With addition of a flavor, the mixture was kneaded in an attritor and then cooled to prepare cream cheese.

TABLE 58

| Cream cheese | Control | Example |
|---|---|---|
| Flesh cream | 100.0 | 50.0 |
| Dextrin (Example 4) | — | 49.8 |

TABLE 58-continued

| Cream cheese | Control | Example |
|---|---|---|
| Water | — | 14.8 |
| Lactobacillus starter | 1.0 | 1.0 |
| Rennet | 0.01 | 0.01 |
| Cheese oil | — | 0.1 |
| Cream flavor | — | 0.1 |
| Dietary fiber | 0.0 | 5.68 |
| Dietary fiber/20 g | 0.0 | 1.14 |
| Caloric val. 1 (KCal/100 g) | 431 | 314 |
| Caloric val. 2 (KCal/100 g) | 431 | 296 |

Example 41

Food example 37

White sauce was prepared according to the recipe of Table 59 by pan-frying soft wheat flour in butter, then mixing other ingredients therewith and boiling down the mixture until the mixture became thickened.

TABLE 59

| White sauce | Control | Example |
|---|---|---|
| Butter | 8.0 | 4.0 |
| Dextrin (Example 3) | — | 4.0 |
| Water | — | 35.9 |
| Soft wheat flour | 12.0 | — |
| Hard wheat flour | — | 9.0 |
| Milk | 65.0 | 32.0 |
| Milk flavor | — | 0.1 |
| Seasoning (liquid) | 13.9 | 13.9 |
| Salt | 1.0 | 1.0 |
| White pepper | 0.1 | 0.1 |
| Dietary fiber | 0.38 | 1.08 |
| Caloric val. 1 (KCal/100 g) | 143 | 91 |
| Caloric val. 2 (KCal/100 g) | 143 | 89 |

Example 42

Food example 38

Meat sauce was prepared according to the recipe of Table 60 by pan-frying minced pork, onions and carrots in fat, pan-frying these ingredients again with addition of wheat flour, admixing other ingredients with the mixture and boiling down the resulting mixture until the mixture became thickened.

TABLE 60

| Meat sauce | Control | Example |
|---|---|---|
| Poke (minced) | 10.0 | 10.0 |
| Fat (cow) | 5.0 | — |
| Dextrin (Example 1) | — | 5.0 |
| Water | 16.0 | 16.0 |
| Onion | 28.2 | 28.2 |
| Carrot | 6.0 | 6.0 |
| Tomato ketchap | 8.5 | 8.5 |
| Tomato puree | 8.5 | 8.5 |
| Apple (boiled) | 12.5 | 12.5 |
| Sugar | 1.7 | 1.7 |
| Salt | 0.8 | 0.8 |
| Spices and seasonings | 1.8 | 1.8 |
| Wheat flour | 1.0 | 1.0 |
| Dietary fiber | 0.95 | 2.65 |
| Dietary fiber/100 g | 0.95 | 2.65 |
| Caloric val. 1 (KCal/100 g) | 110 | 82 |
| Caloric val. 2 (KCal/100 g) | 110 | 79 |

Example 43

Food example 39

Sausage of beef and pork was prepared according to the recipe of Table 61 by crushing raw ingredients to prepare a mixture, filling the mixture into a film bag, allowing the mixture to stand as salt-pickled at 5° C. for 12 hours and thereafter boiling the mixture at 75° C. for 90 minutes, followed by refrigeration.

TABLE 61

| Beef and poke sausage | Control | Example |
|---|---|---|
| Beef | 22.0 | 22.0 |
| Ice | 17.29 | 17.29 |
| Salt | 1.7 | 1.7 |
| Pickles | 0.01 | 0.01 |
| Sugar | 1.0 | 1.0 |
| Sodium glutamate | 0.5 | 0.5 |
| Spices | 0.5 | 0.5 |
| Potato starch | 3.0 | 3.0 |
| Poke (shoulder) | 54.0 | 54.0 |
| Dextrin (Example 1) | — | 10.0 |
| Dietary fiber | 0.20 | 3.60 |
| Dietary fiber/100 g | 0.20 | 3.27 |

Example 44

Food example 40

Corned beef was prepared from beef as held in a salt pickling solution for 5 days and boiled at 115° C. for 90 minutes for the removal of water and fat. According to the recipe shown in Table 62, the other material was admixed with the beef to prepare a uniform mixture, which was then filled into a film bag, sterilized at 75° C. for 60 minutes and thereafter refrigerated.

TABLE 62

| Corned beef | Control | Example |
|---|---|---|
| Beef (pickled and boiled) | 70.0 | 70.0 |
| Fat (cow) | 30.0 | 7.5 |
| Dextrin (Example 3) | — | 15.0 |
| Water | — | 7.5 |
| Dietary fiber | 0.42 | 3.53 |
| Dietary fiber/50 g | 0.21 | 1.77 |
| Caloric val. 1 (KCal/100 g) | 307 | 172 |
| Caloric val. 2 (KCal/100 g) | 307 | 164 |

Example 45

Food example 41

According to the recipe of Table 63, onions and beef were minced and mixed with all the other ingredients, and the mixture was uniformly kneaded and molded. The molded piece was griddled on iron plate at 180° C. over each side for 30 seconds, then boiled at 100° C. for 10 minutes, cooled and thereafter frozen to obtain a frozen hamburger.

TABLE 63

| Hamburg steak | Control | Example |
|---|---|---|
| Processed meat (minced) | 38.8 | 38.8 |
| Fat (cow) | 22.0 | 7.0 |
| Dextrin (Example 3) | — | 14.0 |
| Water | — | 5.0 |
| Onion | 18.0 | 18.0 |
| Fresh crumb | 10.0 | 8.0 |
| Starch | 10.0 | 8.0 |
| Seasonings and spices | 1.2 | 1.2 |
| Dietary fiber | 0.56 | 3.40 |
| Dietary fiber/200 g | 1.12 | 6.80 |
| Caloric val. 1 (KCal/100 g) | 350 | 253 |
| Caloric val. 2 (KCal/100 g) | 350 | 246 |

Example 46

Food example 42

Hamburger putty was prepared according to the recipe of Table 64 by crushing the ingredients into a mixture, filling the mixture into a film bag having a diameter of 8 cm, thereafter freezing the mixture at −30° C. and cutting the mixture into slices, 8 mm in thickness, by a slicer.

TABLE 64

| Hamburger putty | Control | Example |
|---|---|---|
| Beef | 45.0 | 45.0 |
| Poke | 27.5 | 27.5 |
| Fat (cow) | 12.5 | 12.5 |
| Onion | 10.0 | 10.0 |
| Spices | 0.5 | 0.5 |
| Salt | 1.0 | 1.0 |
| Sugar | 1.0 | 1.0 |
| Egg (whole) | 2.5 | 2.5 |
| Dextrin (Example 1) | — | 10.0 |
| Dietary fiber | 0.45 | 3.85 |
| Dietary fiber/60 g | 0.27 | 2.10 |

Example 47

Food example 43

Liver paste was prepared according to the recipe of Table 65 by boiling liver, beef and belly at 100° C. for 5 seconds, then crushing these ingredients, mixing them with the other ingredients, boiling the mixture at 80° C. with full stirring and refrigerating the mixture.

TABLE 65

| Liver paste | Control | Example |
|---|---|---|
| Liver | 28.0 | 28.0 |
| Beef | 10.0 | 10.0 |
| Beef (belly) | 29.69 | 20.5 |
| Lard | 20.0 | 5.0 |
| Dextrin (Example 1) | — | 20.0 |
| Water | — | 4.19 |
| Soup | 8.0 | 8.0 |
| Spices | 2.3 | 2.3 |
| Salt | 2.0 | 2.0 |
| Sodium nitrite | 0.01 | 0.01 |
| Dietary fiber | 0.41 | 7.15 |
| Dietary fiber/30 g | 0.12 | 2.15 |
| Caloric val. 1 (KCal/100 g) | 341 | 226 |
| Caloric val. 2 (KCal/100 g) | 341 | 216 |

Example 48

Food example 44

The dough ingredients listed in Table 66 were fully kneaded together, then fermented at 40° C. for 30 minutes in a heat-insulated device and cut into pieces of suitable size, which were spread out with a needle rod. The ingredients for a pizza sauce were thoroughly mixed together and used after standing for at least 1 hour. The sauce was applied to pizza crust followed by baking in an oven at about 230° C. for 12 minutes to prepare pizza.

TABLE 66

| Pizza (8 sheets) | Control | Example |
|---|---|---|
| Hard wheat flour | 300.0 | 300.0 |
| Soft wheat flour | 200.0 | 200.0 |
| Dried yeast | 10.0 | 10.0 |
| Egg (whole) | 100.0 | 100.0 |
| Water | 180.0 | 180.0 |
| Salt | 8.0 | 8.0 |
| Olive oil | 18.0 | 18.0 |
| Sugar | 2.0 | 2.0 |
| Tomato (boiled) | 400.0 | 340.0 |
| Tomato paste | 10.5 | 10.5 |
| Garlic | 15.0 | 15.0 |
| Salt | 5.2 | 5.2 |
| Spices | 2.0 | 2.0 |
| Olive oil | 30.0 | 30.0 |
| Dextrin (Example 4) | — | 60.0 |
| Dietary fiber | 14.1 | 20.5 |

TABLE 66-continued

| Pizza (8 sheets) | Control | Example |
| --- | --- | --- |
| Dietary fiber/sheet | 1.76 | 2.56 |

Example 49

Food example 45

An omelet was prepared according to the recipe of Table 67 by dissolving indigestible dextrin in milk, admixing the solution with eggs along with the other ingredients and pan-frying the mixture in salad oil.

TABLE 67

| Omelet | Control | Example |
| --- | --- | --- |
| Egg (whole) | 90.0 | 90.0 |
| Milk | 30.0 | 20.0 |
| Salt | 1.0 | 1.0 |
| Pepper | 0.2 | 0.2 |
| Salad oil | 3.0 | 3.0 |
| Butter | 4.0 | 4.0 |
| Dextrin (Example 4) | — | 10.0 |
| Dietary fiber | 0.15 | 1.27 |

Example 50

Food example 46

The materials listed in Table 68 were crushed and mixed together in a raw state to obtain a meat pie ingredient, which was then wrapped with pie dough, followed by baking in an oven at 200° C. for about 30 minutes until the baked mass became colored by scorching to prepare a meat pie.

TABLE 68

| Filling of meat pie | Control | Example |
| --- | --- | --- |
| Poke (minced) | 20.0 | 20.0 |
| Lard | 23.0 | 6.0 |
| Butter | 3.0 | 1.5 |
| Dextrin (Example 1) | — | 13.0 |
| Water | — | 20.5 |
| Milk | 30.0 | 15.0 |
| Milk flavor | — | 0.1 |
| Crumb | 14.5 | 14.5 |
| Egg (whole) | 8.0 | 8.0 |
| Spices | 0.3 | 0.2 |
| Salt | 1.2 | 1.2 |
| Dietary fiber | 0.46 | 4.85 |
| Dietary fiber/50 g | 0.23 | 2.43 |
| Caloric val. 1 (KCal/100 g) | 330 | 209 |
| Caloric val. 2 (KCal/100 g) | 330 | 202 |

Example 51

Food example 47

A steamed Chinese dumpling stuffed with minced pork and frozen was prepared according to the recipe of Table 69 by mincing the vegetables listed, mixing them with the other materials after removal of water to obtain an inner ingredient, and wrapping the ingredient with a covering, followed by steaming at 100° C. for 5 minutes, then by cooling and thereafter by freezing.

TABLE 69

| Filling of Chinese dumpling | Control | Example |
| --- | --- | --- |
| Poke (minced) | 20.0 | 20.0 |
| Lard | 10.0 | 4.0 |
| Dextrin (Example 3) | — | 3.5 |
| Water | — | 2.5 |
| Chinese cabage | 16.0 | 16.0 |
| Cabage | 25.0 | 25.0 |
| Welsh onion | 7.0 | 7.0 |
| Onion | 14.0 | 14.0 |

TABLE 69-continued

| Filling of Chinese dumpling | Control | Example |
| --- | --- | --- |
| Seasonings and spices | 8.0 | 8.0 |
| Dietary fiber | 0.88 | 1.60 |
| Dietary fiber/80 g | 0.70 | 1.28 |
| Caloric val. 1 (KCal/100 g) | 163 | 126 |
| Caloric val. 2 (KCal/100 g) | 163 | 124 |

Example 52

Food example 48

According to the recipe of Table 70, ground fish meat, salt and a small amount of ice were mixed together, the mixture was broken and agitated for 5 minutes by a silent cutter, and the other materials and the remaining amount of ice were added to the resulting mixture and mixed therewith for 10 minutes. When the mixture became thickened or viscous at 15° C., the mixture was molded and fried in oil at 160° C. for 4 minutes to obtain fried kamaboko.

TABLE 70

| Kamaboko | Control | Example |
| --- | --- | --- |
| Surimi | 65.0 | 65.0 |
| Salt | 1.8 | 1.8 |
| Ice | 25.4 | 25.4 |
| Starch | 6.0 | 6.0 |
| Seasonings | 1.8 | 1.8 |
| Dextrin (Example 1) | — | 5.0 |
| Dietary fiber | 0.65 | 2.35 |
| Dietary fiber/120 g | 0.78 | 2.82 |

Example 53

Food example 49

A blackberry liquor was prepared according to the recipe of Table 71 by immersing blackberries in distilled spirits for 40 days, discarding the blackberries and then aging the spirits for 2 months.

TABLE 71

| Black berry liquor | Control | Example |
| --- | --- | --- |
| Black berry | 57.0 | 57.0 |
| Sugar | 34.2 | 15.0 |
| Dextrin (Example 2) | — | 19.1 |
| Aspartame | — | 0.1 |
| White liquor (70 proof) | 65.8 | 65.8 |
| Dietary fiber | 0 | 5.04 |
| Dietary fiber/100 g | 0 | 5.04 |

Example 54

Feed example 1

Dog food was prepared according to the recipe of Table 72.

TABLE 72

| Dog food | Control | Example |
| --- | --- | --- |
| Corn | 25.0 | 25.0 |
| Wheat and wheat flour | 24.0 | 24.0 |
| Born and meat meal | 16.3 | 16.3 |
| Soy bean waste | 14.4 | 14.4 |
| Fish meal | 4.8 | 4.8 |
| Wheat germ | 2.9 | 2.9 |
| Yeast | 2.9 | 2.9 |
| Animal fat | 3.8 | 3.8 |
| Vitamins and minerals | 5.9 | 5.9 |
| Dextrin (Example 1) | — | 10.0 |
| Dietary fiber | 4.70 | 8.10 |

Example 55

Feed example 2
Cat food was prepared according to the recipe Table 73.

TABLE 73

| Cat food | Control | Example |
| --- | --- | --- |
| Corn | 28.4 | 28.4 |
| Wheat flour | 27.3 | 27.3 |
| Brewer's yeast | 3.3 | 3.3 |
| Malt | 3.3 | 3.3 |
| Soy bean waste | 16.4 | 16.4 |
| Fish meal | 0.5 | 0.5 |
| Meat meal | 18.6 | 18.6 |
| Vitamins and minerals | 2.2 | 2.2 |
| Dextrin (Example 1) | — | 10.0 |
| Dietary fiber | 5.43 | 8.83 |

Example 56

Feed example 3
A feed for pigs was prepared according to the recipe of Table 74.

TABLE 74

| Pig feed | Control | Example |
| --- | --- | --- |
| Corn | 75.0 | 75.0 |
| Soy bean waste | 11.0 | 11.0 |
| Bran | 3.0 | 3.0 |
| Fish meal | 9.0 | 9.0 |
| Calcium tri-phosphate | 0.7 | 0.7 |
| Calcium carbonate | 0.6 | 0.6 |
| Salt | 0.3 | 0.3 |
| Vitamins | 0.2 | 0.2 |
| Minerals | 0.2 | 0.2 |
| Dextrin (Example 1) | — | 10.0 |
| Dietary fiber | 6.95 | 10.4 |

Example 57

Feed example 4
A feed for broilers in the initial stage was prepared according to the recipe of Table 75.

TABLE 75

| Feed for broiler | Control | Example |
| --- | --- | --- |
| Corn | 44.65 | 44.65 |
| Milo | 10.0 | 10.0 |
| Soy bean waste | 23.0 | 23.0 |
| Fish meal | 9.0 | 9.0 |
| Gluten meal | 3.0 | 3.0 |
| Alfalfa meal | 2.0 | 2.0 |
| Corn distiller's dried solubles | 1.0 | 1.0 |
| Animal fat | 5.1 | 5.1 |
| Salt | 0.25 | 0.25 |
| Calcium carbonate | 0.6 | 0.6 |
| Calcium di-phosphate | 0.8 | 0.8 |
| Lysine | 0.05 | 0.05 |
| Methionine | 0.18 | 0.18 |
| Vitamins | 0.1 | 0.1 |
| Choline chloride | 0.05 | 0.05 |
| Minerals | 0.1 | 0.1 |
| Nicarbazin | 0.05 | 0.05 |
| Oxytetracycline | 0.07 | 0.07 |
| Dextrin (Example 1) | — | 10.0 |
| Dietary fiber | 7.54 | 10.9 |

Example 58

Feed example 5
A feed for laboratory rats was prepared according to the recipe of Table 76.

TABLE 76

| Feed for laboratory rat | Control | Example |
| --- | --- | --- |
| Wheat | 12.4 | 12.4 |
| Oat | 18.6 | 18.6 |
| Corn | 10.3 | 10.3 |
| Barley | 34.1 | 34.1 |
| Bran | 3.1 | 3.1 |
| Fish meal | 6.3 | 6.3 |
| Skimmed milk powder | 1.0 | 1.0 |
| Alfalfa | 1.6 | 1.6 |
| Molass | 1.0 | 1.0 |
| Vitamins and minerals | 0.5 | 0.5 |
| Others | 11.1 | 11.1 |
| Dextrin (Example 1) | — | 10.0 |
| Dietary fiber | 6.22 | 9.62 |

What we claim is:

1. An indigestible dextrin characterized in that the dextrin is prepared by heat-treating potato starch with addition of hydrochloric acid thereto to obtain a pyrodextrin, hydrolyzing the pyrodextrin with alpha-amylase and glucoamylase and removing at least one-half of glucose formed from the resulting hydrolyzate, and comprises a fraction other than glucose, (A) said fraction containing at least 80% of an indigestible component, (B) said Fraction containing 30 to 35% of glucose residues having a 1→4 glycosidic linkage only, (C) said fraction having a number average molecular weight of 510 to 965, (D) said fraction having a number average molecular weight Y calculated 1 the equation:

$$Y = -293 + 106.004 \cdot X$$

wherein X is the amount (in % based on said fraction) of glucose residues having both 1→4 and 1→6 glycosidic linkages as quantitatively determined by "Hakomori's methylation method," said calculated value Y being in the range of variations of up to 20% from the number average molecular weight as actually measured, (E) the ratio of the weight average molecular weight of said fraction to the number average molecular weight thereof being at least 25:1.

2. An indigestible dextrin as defined in claim 1 which contains up to 35% of glucose and at least 37% of an indigestible component.

3. An indigestible dextrin as defined in any one of claims 1 to 2 wherein said fraction that has been separated from glucose contains at least 18% of dietary fiber and which is including glucose contains at least 7.8% of dietary fiber.

4. An indigestible dextrin as defined in any one of claims 1 to 2 wherein said fraction that has been separated from glucose is up to 2 kcal/g in caloric value 1 and which is containing glucose is up to 3.11 kcal/g in caloric value 1.

5. An indigestible dextrin as defined in any one of claims 1 to 2 wherein said fraction that has been separated from glucose is up to 1.5 kcal/g in caloric value 2 and which in including glucose is up to 2.9 kcal/g in caloric value 2.

6. An indigestible dextrin as defined in claim 1 which has activity to diminish serum lipids.

7. An indigestible dextrin as defined in claim 1 which has activity to improve the intestine.

8. An indigestible dextrin as defined in claim 1 which has hypotensive activity.

9. An indigestible dextrin as defined in claim 1 which has activity to prevent cancer of the large intestine.

10. An indigestible dextrin as defined in claim 1 which has activity to reduce the insulin secretion.

11. A food containing an indigestible dextrin as defined in claim 1.

12. A food as defined in claim 11 which is a candy, cake, bakery product, ice, snack, beverage or yogurt.

13. A food as defined in claim 11 which is a soup, mayonnaise, dressing, processed livestock meat product or processed fishery product.

14. A food containing an indigestible dextrin as defined in claim 2.

* * * * *